(12) United States Patent
Chandra et al.

(10) Patent No.: US 10,761,206 B2
(45) Date of Patent: Sep. 1, 2020

(54) SOIL MEASUREMENT SYSTEM USING WIRELESS SIGNALS

(71) Applicant: Microsoft Technology Licensing, LLC, Redmond, WA (US)

(72) Inventors: Ranveer Chandra, Kirkland, WA (US); Jian Ding, Houston, TX (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 148 days.

(21) Appl. No.: 16/154,483

(22) Filed: Oct. 8, 2018

(65) Prior Publication Data
US 2020/0110170 A1 Apr. 9, 2020

(51) Int. Cl.
*G01S 13/88* (2006.01)
*G01V 3/12* (2006.01)
(Continued)

(52) U.S. Cl.
CPC .......... *G01S 13/885* (2013.01); *G01N 33/246* (2013.01); *G01S 13/88* (2013.01);
(Continued)

(58) Field of Classification Search
CPC ........ G01S 13/00; G01S 13/88; G01S 13/885; G01N 33/00; G01N 33/24; G01N 33/246;
(Continued)

(56) References Cited

U.S. PATENT DOCUMENTS 4,059,499 A * 11/1977 Ibsen Nielsen .... G01N 27/3335
204/418

5,033,397 A * 7/1991 Colburn, Jr. ......... A01B 79/005
111/118
(Continued)

FOREIGN PATENT DOCUMENTS

| JP | H0438414 A | 2/1992 |
|---|---|---|
| JP | H04128683 A | 4/1992 |
| WO | 2005069021 A1 | 7/2005 |

OTHER PUBLICATIONS

Friis, Herald T.,"A Note on a Simple Transmission Formula", In Proceedings of the IRE,vol. 34, Issue 5, May 1946, pp. 254-256.
(Continued)

*Primary Examiner* — Hoai-An D. Nguyen
(74) *Attorney, Agent, or Firm* — Alleman Hall Creasman & Tuttle LLP

(57) ABSTRACT

A soil measurement system is provided, comprising a soil surveying device, a radio receiver, a plurality of subterranean antennas, and a processor. The soil surveying device comprises a wireless radio transmitter configured to emit a wireless signal at a predetermined bandwidth in a predetermined spectrum. The plurality of subterranean antennas are in an array electronically connected to the radio receiver and configured to be mounted in a subterranean environment at different depths in the subterranean environment. Each of the plurality of subterranean antennas is configured to receive the wireless signal at a respective point in time. The processor is configured to determine a relative time of flight of the received wireless signal between the plurality of antennas at the respective point in time, and estimate a soil permittivity based on the determined relative time of flight. The measurement system may be applied to materials other than soil, in some examples.

20 Claims, 23 Drawing Sheets

(51) Int. Cl.
| | |
|---|---|
| G01N 33/24 | (2006.01) |
| G01N 13/02 | (2006.01) |
| H04B 13/02 | (2006.01) |
| G01N 27/02 | (2006.01) |
| G01N 27/04 | (2006.01) |

(52) U.S. Cl.
CPC .............. *G01V 3/12* (2013.01); *H04B 13/02* (2013.01); *G01N 27/026* (2013.01); *G01N 27/043* (2013.01)

(58) Field of Classification Search
CPC .. G01N 2033/245; G01N 27/00; G01N 27/02; G01N 27/026; G01N 27/04; G01N 27/043; G01N 27/048; A01G 25/00; A01G 25/16; A01G 25/167; G01V 3/00; G01V 3/12; H04B 13/00; H04B 13/02; A01B 47/00; A01B 79/00; A01B 79/02
USPC ....... 324/600, 629, 634, 637, 639, 640, 642, 324/643; 340/500, 540, 601, 602
See application file for complete search history.

(56) References Cited

U.S. PATENT DOCUMENTS

| | | | | |
|---|---|---|---|---|
| 7,482,820 | B1* | 1/2009 | Campbell ............ | G01N 27/223 324/644 |
| 8,035,403 | B1 | 10/2011 | Campbell et al. | |
| 8,308,077 | B1* | 11/2012 | Campbell ............ | A01G 25/167 239/11 |
| 8,340,910 | B1* | 12/2012 | Magro .................... | A01G 7/00 702/2 |
| 8,947,102 | B1* | 2/2015 | Evett .................... | G01N 27/223 324/600 |
| 10,073,074 | B1* | 9/2018 | Kumar ................. | G01N 27/043 |
| 10,470,243 | B2* | 11/2019 | Sundaresan ......... | H04W 72/082 |
| 2015/0181315 | A1* | 6/2015 | Vuran .................. | G01S 13/885 340/870.3 |
| 2016/0187524 | A1 | 6/2016 | Suhami | |
| 2017/0023541 | A1 | 1/2017 | Ellegaard et al. | |
| 2017/0108452 | A1 | 4/2017 | Carlson | |
| 2018/0049694 | A1* | 2/2018 | Singh Alvarado ..... | A61B 5/681 |
| 2018/0088222 | A1* | 3/2018 | Anholt .................... | G01S 13/08 |

OTHER PUBLICATIONS

"Soil Moisture Monitoring: A Selection Guide", Retrieved from: https://www.agric.wa.gov.au/horticulture/soil-moisture-monitoring-selection-guide, Aug. 22, 2019, 9 Pages.
Curtis, et al., "Moisture Effects on the Dielectric Properties of Soils", In Proceedings of IEEE Transactions on Geoscience and Remote Sensing,vol. 39, Issue 1, Jan. 2001, pp. 125-128.
Daskalakis, et al., "Soil Moisture Scatter Radio Networking with Low Power", In Proceedings of IEEE Transactions on Microwave Theory and Techniques,vol. 64, Issue 7, Jun. 13, 2016, pp. 2338-2346.
Dey, et al., "Electromagnetic Characterization of soil Moisture and Salinity for uhf rfid Applications in Precision Agriculture", In Proceedings of 46th European Microwave Conference, Oct. 4, 2016, pp. 616-619.
Dobson, et al., "Active Microwave Soil Moisture Research", In Proceedings of IEEE Transactions on Geoscience and Remote Sensing, Jan. 1986, 61 Pages.
Dobson, et al., "Microwave Dielectric Behavior of Wet Soil Part II: Dielectric Mixing Models", In Proceedings of IEEE Transactions on Geoscience and Remote Sensing, Jan. 1, 1985, pp. 35-46.
Gjengset, et al., "Phaser: Enabling Phased Array Signal Processing on Commodity wifi Access Points", In Proceedings of the 20th annual International conference on Mobile computing and networking, Sep. 7, 2014, 12 Pages.
Grisso, et al., "Precision Farming Tools: Soil Electrical Conductivity", Retrieved from: https://vtechworks.lib.vt.edu/bitstream/handle/10919/51377/442-508.pdf?sequence=1&isAllowed=y , 2005, 6 Pages.
Halperin, et al., "Tool Release: Gathering 802.11n Traces with Channel State Information", In ACM SIGCOMM Computer Communication Review, vol. 41, Issue 1, Jan. 22, 2011, 1 Page.
Hasan, et al., "A Monopole-coupled RFID Sensor for Pervasive Soil Moisture Monitoring", In Proceedings of 2013 IEEE Antennas and Propagation Society International Symposium, Jul. 7, 2013, 2 Pages.
Hilhorst, M.A., "A Pore Water Conductivity Sensor", In Journal of Soil Science Society of America, Nov. 2000, 2 Pages.
Huisman, et al., "Measuring Soil Water Content with Ground Penetrating Radar", In Vadose Zone Journal,vol. 2, Issue 4, Nov. 1, 2003, pp. 476-491.
Islam, et al., "Implementation of Sensor RFID: Carrying Sensor Information in the Modulation Frequency", In Proceedings of IEEE Transactions on Microwave Theory and Techniques,vol. 63, Issue 8, Jun. 29, 2015, 11 Pages.
Jol, Harry M., "Ground Penetrating Radar Theory and Applications" In Publication of Elsevier, Dec. 8, 2008, 540 Pages.
Kaplan, et al., "Understanding GPS: Principles and Applications", In Publication of Artech house, 2005, 11 Pages.
Kotaru, "Spotfi: Decimeter Level Localization Using Wifi", In Proceedings of the 2015 ACM Conference on Special Interest Group on Data Communication, Aug. 17, 2015, pp. 269-282.
Kumar, et al., "Accurate Indoor Localization with Zero Start-up Cost", In Proceedings of the 20th annual International conference on Mobile computing and networking, Sep. 7, 2014, pp. 483-494.
Mohanty, et al., "Soil Moisture Remote Sensing: State-of-the-science", In Vadose Zone Journal,vol. 16, Issue 1 Jan. 1, 2017, 9 Pages.
"International Search Report and Written Opinion Issued in PCT Application No. PCT/US2019/049409", dated Dec. 13, 2019, 10 Pages.
Peters, et al. "Practical use of soil Moisture Sensors for Irrigation Scheduling",Retrieved From: https://research.libraries.wsu.edu/xmlui/bitstream/handle/2376/4389/FS083E.pdf?sequence=2, 2013, 6 Pages.
Priyantha, et al., "The Cricket Location-Support System", In Proceedings of the 6th International Conference on Mobile Computing and Networking, Aug. 1, 2000, 12 Pages.
Richards, "Soil MoistureTensiometer Materials and Construction", In Journal of Soil Science, vol. 53, Issue 4, Apr. 1, 1942, pp. 241-248.
Robinson, et al., "A Review of Advances in Dielectric and Electrical Conductivity Measurement in Soils Using time Domain Reflectometry", In Journal of Vadose Zone,vol. 2, Issue 4, 2003, pp. 444-475.
Robinson, et al., "Soil Moisture Measurement for Ecological and Hydrological Watershed-scale Observatories: A Review", In Journal of Vadose Zone,vol. 7, Issue 1, Feb. 1, 2008, pp. 358-389.
Roth, et al., "Calibration of Time Domain Reflectometry for Water Content Measurement using a Composite Dielectric Approach", In Journal of Water Resources Research,vol. 26, Issue 10, Oct. 26,1990, pp. 2267-2273.
Saarenketo, Timo, "Electrical Properties of Water in Clay and Silty Soils", In Journal of Applied Geophysics, vol. 40, Issue 1-3, Oct. 1, 1998, pp. 73-88.
Smola, et al., "A Tutorial on Support Vector Regression", In Journal of Statistics and computing,vol. 14, Issue 3, Aug. 1, 2004, 24 Pages.
Sun, et al., "Dynamic Connectivity in Wireless Underground Sensor Networks", In Proceedings of IEEE Transactions on Wireless Communications,vol. 10, Issue 12, Oct. 13, 2011, 27 Pages.
Vasisht, et al., "Decimeter-level Localization with a Single wifi Access Point", In Proceedings of 13th USENIX Symposium on Networked Systems Design and Implementation, 2016, pp. 165-178.
Vasisht, et al., "Farmbeats: An iot Platform for Data-Driven Agriculture", In Proceedings of the 14th USENIX Symposium on Networked Systems Design and Implementation, Mar. 27, 2017, pp. 515-529.
Vuran, et al., "Communication Through Soil in Wireless Underground Sensor Networks—theory and practice", In Sensor Networks, 2010, pp. 309-347.

(56) References Cited

OTHER PUBLICATIONS

Wang, et al., "Remote Sensing of Soil Moisture Content, over bare field at 1.4 ghz frequency", In Journal of Geophysical Research, vol. 86, Issue C6, Jun. 20, 1980, 26 Pages.

Ward, et al., "A New Location Technique for the Active Office", In IEEE Personal Communications, vol. 4, Issue 5, Oct. 1997, 11 Pages.

Xie, et al., "Precise power delay profiling with commodity wifi", In Proceedings of the 21st Annual International Conference on Mobile Computing and Networking, Sep. 7, 2015, pp. 53-64.

Xiong, et al., "Arraytrack: a finegrained indoor location system", In Proceedings of 10th USENIX Symposium on Networked Systems Design and Implementation, 2013, pp. 71-84.

Xiong, et al., "Tonetrack: Leveraging Frequency-agile Radios for time-based Indoor Wireless Localization", In Proceedings of the 21st Annual International Conference on Mobile Computing and Networking, Sep. 7, 2015, pp. 537-549.

Ding, et al., "Estimating Soil Moisture and Electrical Conductivity Using Wi-Fi", Retrieved From: https://www.microsoft.com/en-us/research/uploads/prod/2018/10/SMURF_TR-1.pdf, Oct. 2018, 15 Pages.

Schmidt, Ralph, "Multiple Emitter Location and Signal Parameter Estimation", In Proceedings of IEEE Transactions on Antennas and Propagation, vol. 34, Issue 3, Mar. 1986, 5 Pages.

Noborio. K, "Measurement of Soil Water Content and Electrical Conductivity by Time Domain Reflectometry: a Review", In Journal of Computers and Electronics in Agriculture, May, 2001, 25 Pages.

\* cited by examiner

FIG. 8C SILT LOAM
FIG. 8B SANDY LOAM
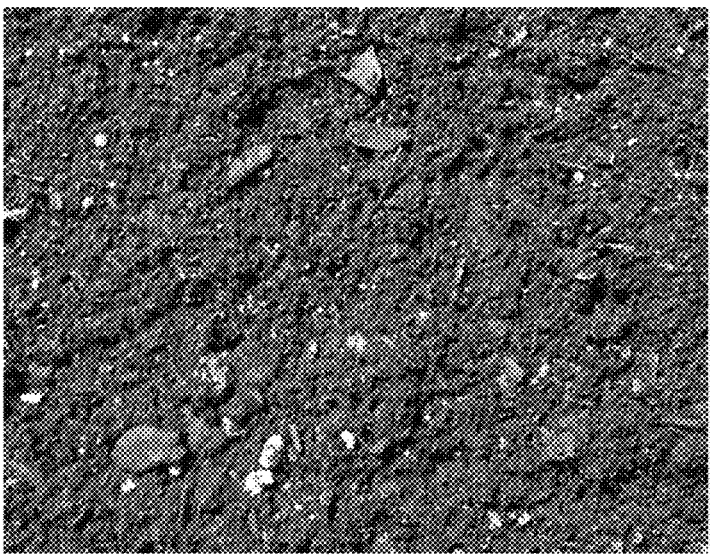
FIG. 8A POTTING MIX

SOIL MEASUREMENT SYSTEM USING WIRELESS SIGNALS

BACKGROUND

Soil moisture and soil electrical conductivity (EC) of a farm are important parameters for data-driven farming. This knowledge can help a farmer improve crop yield, reduce costs, and practice sustainable agriculture.

Several agricultural applications rely on soil moisture and soil EC measurements. For example, precision irrigation, which refers to the variable application of water in different regions of the farm, depends on accurate soil moisture values at different depths. This helps reduce the amount of water use, and also reduces the leeching of ground water by the contaminants used in fertilizers and other agricultural inputs. Soil EC is another key indicator of soil health. It has been shown to correlate very well with crop yield and plant nutrient availability, and farmers are recommended by the United States Department of Agriculture (USDA) to measure soil EC to determine soil treatment plans and management zones for Precision Agriculture. However, numerous challenges exist, as discussed below, in providing a cost-effective, widely adoptable technological solution that effectively measures soil moisture and soil EC.

SUMMARY

A soil measurement system is provided, comprising a soil surveying device, a radio receiver, a plurality of subterranean antennas, and a processor. The soil surveying device comprises a wireless radio transmitter configured to emit a wireless signal at a predetermined bandwidth in a predetermined spectrum. The plurality of subterranean antennas are in an array electronically connected to the radio receiver and configured to be mounted in a subterranean environment at different depths in the subterranean environment. Each of the plurality of subterranean antennas is configured to receive the wireless signal at a respective point in time. The processor is configured to determine a relative time of flight of the received wireless signal between the plurality of antennas at the respective point in time, and estimate a soil permittivity based on the determined relative time of flight.

According to another aspect, a measurement system is provided similar to that described above, which measures permittivity in mediums not limited to soil.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

FIGS. 8A-8C illustrate the different soil types used in the experimental examples.

DETAILED DESCRIPTION

Figure 1:
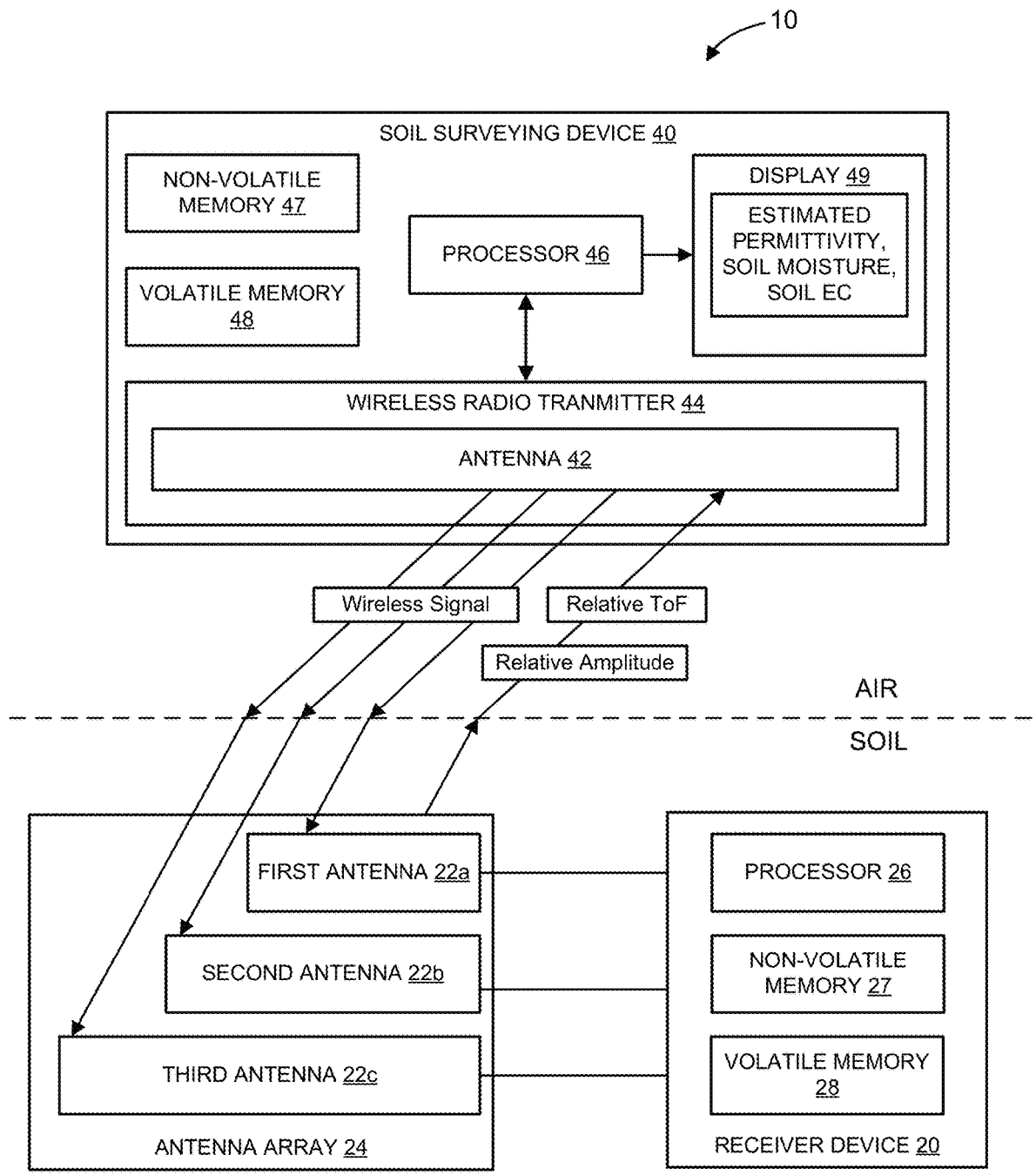
FIG. 1 shows a soil measurement system according to one implementation of the present disclosure.

The inventors have surveyed the state of the art and identified several techniques over the last few decades that attempt to measure soil moisture and EC. These methods include direct sensing techniques that require soil to be extracted and dried out, as well as indirect sensing methods that measure surrogate properties of soil moisture and EC, such as capacitance, electrical, and nuclear response. Radar-based technologies also exist to measure soil moisture and EC.

The most accurate method for soil sensing is the direct gravimetric method of sampling soil, drying out the soil, and weighing the amount of moisture that is lost from the soil. However, this technique is expensive, manual, requires oven drying, and disturbs the soil.

Several lower-cost surrogate sensing approaches have been proposed in the conventional art that estimate soil moisture based on the indirect properties of soil that are affected by moisture. For example, electrical resistance-based sensors measure the resistance of soil when current is passed through two electrodes. Capacitive sensors measure the time to charge the capacitor. A calibration chart is then used to convert the resistance to the corresponding soil moisture value. Heat-diffusion sensors measure the rate of increase of temperature when applying a heat source. Wet soil dissipates heat much faster than dry soil. Tensiometers measure the tension created by soil absorbing the water kept in a ceramic cup connected through a tube. Radioactive sensors measure the slowing of neutrons in soil after being emitted into the soil from a fast-neutron source. To measure EC, the resistance to current is measured through electrodes in soil.

However, one of the key challenges in the adoption of soil moisture and EC sensing technologies is the cost of existing sensor solutions. Indeed, the high cost of commercial soil moisture and EC sensors has limited their adoption. Most commercial grade soil moisture sensors, such as those available from DECAGON, CAMPBELL SCIENTIFIC, or SENSOTERRA, typically cost over one hundred U.S. dollars. Even the least expensive commercial grade soil moisture or soil EC sensing solutions still cost over one hundred dollars. They use ruggedized components that typically measure the resistance, capacitance, or conductivity change of the sensor. Although hobbyist soil moisture sensors are available for less than 10 U.S. dollars, they are not reliable and degrade quickly, and are consequently not used by agricultural experts. The cost of the sensor package is further increased by the need for additional components, such as the microprocessor, Radiofrequency (RF) modules, ADC, cables, packaging, etc.

At these price points for soil sensors, it is unaffordable for most farmers to adopt moisture or EC sensing technologies. Most farmers in developing regions do not make enough to afford sensors that cost a few hundred dollars. In fact, even in the developed world, the cost of these sensors has limited the adoption of precision irrigation technologies.

Even though prior work on Ground Penetrating Radars (GPRs) has considered using RF for measuring soil properties, these systems are specialized, wideband (a few GHz in the lower UHF spectrum), and hence cost several thousands of dollars.

Previous GPR techniques use time of flight (ToF) to measure the speed of the RF signal, and consequently the permittivity of soil. They use wideband spectrum from 100s of MHz to few GHz of spectrum to measure ToF. However, such a wide contiguous bandwidth is not available in the unlicensed spectrum. Furthermore, ToF measures the average moisture level from the surface of soil, but does not measure the absolute moisture levels, such as the soil moisture 8 inches below surface level.

Accurate ToF and signal attenuation measurements are the key factors for the accuracy of soil moisture and EC estimation, which imposes a need of special system design to give reliable results. The cost of RF sensing systems is thus usually very high, of the order of several thousand dollars. ToF estimation requires ultra-wide bandwidth to obtain good performance. The bandwidth of systems like GPRs usually spans multiple GHz. Such systems also require specially designed hardware to allow operation on a wide bandwidth. The United States Federal Communications Commission (FCC)-imposed power limit for ultra-wideband systems, which is -41.3 dBm/MHz, gives rise to higher power efficiency requirements in designing these systems.

Since EC estimation requires absolute amplitude measurements, it makes the system complex. One needs to know system parameters both during design and in operation. For Time-Domain Reflectometry (TDR) systems that use transmission line to estimate permittivity and EC, tradeoffs exist when choosing probe design parameters for ToF and EC. In antenna-based systems like GPRs, besides the system parameters given for A as follows from the Friis transmission equation, the whole propagation path from transmitter to receiver, which includes multiple reflections and refractions, also needs to be carefully modeled.

ToF-based RF sensing techniques, such as GPRs and TDRs, exploit the relationship between electromagnetic (EM) wave characteristics and material properties. Two key material properties that enable RF-based sensing are dielectric permittivity and EC. Compared with wave propagation in free space, larger permittivity and EC values in soils add attenuation to the signal strength and slow down the wave propagation speed. Conversely, knowing the attenuation and velocity of a signal traveling in a soil can help to figure out the permittivity and EC of that soil. Next, the relationship between material properties and wave propagation will be mathematically explained.

Permittivity, $\varepsilon^* = \varepsilon' + j\varepsilon''$, is a complex value, where $\varepsilon'$ and $\varepsilon''$ are its real and complex components. It is usually represented by the term relative permittivity given as:

$$\varepsilon_r^* = \frac{\varepsilon^*}{\varepsilon_0} = \frac{\varepsilon'}{\varepsilon_0} + j\frac{\varepsilon''}{\varepsilon_0} = \varepsilon_r' + j\varepsilon_r'' \qquad (1)$$

In Equation (1), $\varepsilon_0$ is the permittivity of free space ($8{:}854 \times 10^{-12}$ F/m). EC is usually represented by a real value, $\sigma$, since its imaginary component is insignificant at radio frequencies.

Permittivity (in F/m) and EC (in S/m) affect attenuation and phase rotation for a signal that propagates in a conducting dielectric medium at frequency f and travels a distance of d in the following form:

$$E(f, d) = \frac{A}{d} e^{-(\alpha + j\beta)d} \qquad (2)$$

$$\alpha = \frac{2\pi f}{c} \sqrt{\frac{\varepsilon_r'}{2}\left[\sqrt{1 + \left(\frac{\varepsilon_r'' + \frac{\sigma}{2\pi f \varepsilon_0}}{\varepsilon_r'}\right)^2} - 1\right]} \qquad (3)$$

$$\beta = \frac{2\pi f}{c} \sqrt{\frac{\varepsilon_r'}{2}\left[\sqrt{1 + \left(\frac{\varepsilon_r'' + \frac{\sigma}{2\pi f \varepsilon_0}}{\varepsilon_r'}\right)^2} + 1\right]} \qquad (4)$$

In Equations (2)-(4), $\alpha$ and $\beta$ are the attenuation coefficient that determines signal attenuation and the phase coefficient that determines phase variation during propagation, respectively. It will be appreciated that c is the speed of light and A is the signal amplitude determined by wavelength in the medium and system parameters including antenna beam pattern, gain settings at transmitter and receiver, and antenna gains.

For isotropic antennas, A is given as follows from the Friis equation:

$$A = \frac{\sqrt{P_t G_t G_r} \lambda}{4\pi} \qquad (5)$$

In Equation (5), $P_t$ is the transmit power, and $G_t$ and $G_r$ are the transmit and receive antenna gains, respectively. The wave propagation in free space is given as:

$$E_0(f, d) = \frac{A_0}{d} e^{j\frac{2\pi f d}{c}} = \frac{\lambda_0 A}{\lambda_d} e^{-(\alpha_0 + j\beta_0)d} \qquad (6)$$

In Equation (6), $\alpha_0 = 0$ and $\beta_0 = 2\pi f/c$. Here, the dielectric medium basically adds an extra attenuation due to the change of wavelength $\lambda_0/\lambda$ and the transmission loss $e^{\alpha d}$, and slows down the speed of wave by a factor of $\beta/\beta_0$. The propagation velocity can be expressed as follows:

$$v = \frac{c}{\beta/\beta_0} = \frac{c}{\sqrt{K_a}} \qquad (7)$$

$$K_a = \frac{\varepsilon_r'}{2}\left[\sqrt{1 + \left(\frac{\varepsilon_r'' + \frac{\sigma}{2\pi f \varepsilon_0}}{\varepsilon_r'}\right)^2} - 1\right] \qquad (8)$$

$K_a$ is known as the apparent permittivity of a material, which is often adopted in ToF-based RF techniques to describe the permittivity estimated from ToF. When $\varepsilon''_r$ and $\sigma/2\pi f \varepsilon_0$ are small compared with $\varepsilon'_r$, the above equation reduces to:

$$K_a = \varepsilon'_r \quad (9)$$

The typical range of $\sqrt{K_a}$ in soil is 2-6, corresponding to 2-6 times slowdown of wave speed in soil compared with the speed of light.

ToF-based RF techniques measure ToF to estimate wave velocity v and then determine the apparent permittivity $K_a$ of soil. The relationship between $K_a$ and ToF of a signal traveling through a known distance d is given as follows:

$$K_a = \left(\frac{c\tau}{d}\right)^2 \quad (10)$$

Soil is considered as a mixture of soil particles, water and air. The permittivity of soil strongly depends on the water content in it since water has a much larger permittivity than air and soil particles. The permittivity of water is around 80, while the permittivity of air is 1 and the permittivity of soil particles is from 3 to 10. The water content-permittivity relationship of soils has been well studied and modeled. Once the permittivity value of a soil is obtained, it can be fit into existing water content-permittivity models for that soil type to estimate the water content. An example model, which is widely used for mineral soils, is as follows:

$$\theta = -5.3 \times 10^{-2} + 2.92 \times 10^{-2} K_a - 5.5 \times 10^{-4} K_a^2 + 4.3 \times 10^{-6} K_a^3 \quad (11)$$

In Equation (11), $\theta$ is the volumetric water content in soil and $K_a$ is the soil apparent permittivity.

RF techniques measure the signal attenuation $e^{\alpha d}$ through a known distance d to estimate the attenuation coefficient $\alpha$ and then use $\alpha$ to estimate EC. In attenuation-based EC estimation methods, since both the imaginary component of permittivity $\varepsilon''_r$ and electrical conductivity $\sigma$ contribute to the attenuation, a term apparent conductivity or effective conductivity is used for the EC estimated by such methods, which is given as:

$$\sigma_a = \sigma + 2\pi f \varepsilon_0 \varepsilon''_r \quad (12)$$

Equation (12) can be calculated from Equation (3). When $\sigma_a/2\pi f \varepsilon_0 \varepsilon'_r$ is a small value, the calculation of $\sigma_a$ can be simplified to $$\sigma_a = \frac{\alpha \sqrt{\varepsilon'_r}}{60\pi} \quad (13)$$

In view of the above, the present inventors developed a low-cost soil measurement system, which estimates soil moisture and soil EC without the need for a costly sensor, and can be used to estimate moisture and EC of other mediums as well. Instead, the system utilizes the phenomenon that RF waves travel slower in soil with higher permittivity. With a plurality of antennas in soil or other medium, the system can estimate the permittivity, and the corresponding moisture and EC levels of soil or other medium at the location of the antennas.

Turning to FIG. 1, system 10 comprises a soil surveying device 40, a radio receiver device 20, a plurality of subterranean antennas 22a, 22b, and 22c, and a processor 46 as well as non-volatile memory 47 and volatile memory 48. The soil surveying device 40 may also include a display 49.

The system 10 is configured to measure soil moisture and soil EC using Wi-Fi wireless signals. An antenna 42 on a Wi-Fi wireless radio transmitter 44 on a soil surveying device 40, such as a phone or on a tractor, transmits packets which are received by a plurality of antennas 22a, 22b, and 22c on a radio receiver 20 in the soil. All antennas 22a, 22b, and 22c are connected to a single radio receiver 20. The received signal is used to estimate the permittivity of soil, which is then used to determine the soil moisture and soil EC.

In other words, a soil surveying device 40 comprising a wireless radio transmitter 44 is configured to emit a wireless signal at a predetermined bandwidth in a predetermined spectrum. The predetermined spectrum is preferably 2.4 GHz, and the predetermined bandwidth is preferably 70 MHz, although 80 MHz or other suitable bandwidth range could be utilized. A plurality of subterranean antennas 22a, 22b, and 22c in an antenna array 24 are electronically connected to the radio receiver 20 and configured to be mounted in a subterranean environment at different depths in the subterranean environment. Each of the plurality of subterranean antennas 22a, 22b, and 22c is configured to receive the wireless signal at a respective point in time. The radio receiver 20 may also be provided with a processor 26, non-volatile memory 27, and volatile memory 28.

The system 10 is configured to sense soil moisture and soil EC using RF propagation in existing Wi-Fi bands. Specifically, the system 10 uses the unlicensed 2.4 GHz of spectrum, with multiple antennas 22a, 22b, and 22c placed at different depths in the soil. A wireless transmitter 44, e.g. Wi-Fi, from the soil surveying device, emits signals that are received by these antennas 22a, 22b, and 22c in the soil. The relative ToF or relative amplitude that are determined may then be transmitted back wirelessly by the multiple antennas 22a, 22b, and 22c, by another transmitter provided on the radio receiver 20, or transmitted by a wired connection to the soil surveying device 40 (which may function as the downstream computing device) housing the wireless radio transmitter 44 or to another downstream computing device. A processor of the radio receiver, the soil surveying device, or another downstream computing device may then compute the soil moisture, soil permittivity, and soil EC at the location of the antennas. This capability of the system 10 enables several new scenarios. For example, a smartphone or tablet computer may be used as the soil surveying device that functions as the downstream computing device, and the wireless transmitter may be a WiFi transmitter equipped in a wireless network interface controller of the smartphone or tablet computer. Thus, a farmer with a Wi-Fi enabled smartphone or tablet computer will be able to learn about the soil in their farm. A tractor or an unmanned aerial vehicle (UAV) equipped with such smartphone or tablet computer devices can create new up-to-date maps of the soil every time they traverse the farm. An EC map can help a farmer build management zones. A sprinkler system can dynamically learn of moisture maps of the farm, and adapt the time of irrigation, and the amount of water that it uses in different regions.

To improve measurements of absolute moisture levels, such as the soil moisture 8 inches below surface level, the system estimates the moisture and EC level from Wi-Fi signals. Due to poor propagation in 5 GHz of spectrum, the system preferably uses the 70 MHz of available spectrum in 2.4 GHz. Instead of measuring the absolute ToF, which would require a wide bandwidth, the system uses a technique to measure the relative ToF of the received signal between multiple antennas. The relative ToF is used to determine the permittivity and soil moisture. The soil EC is subsequently measured using the ratio of signal amplitudes on the different antennas.

In other words, a processor 46 may be configured to determine a relative ToF of the received wireless signal between the plurality of subterranean antennas at the respective point in time, and estimate a soil permittivity based on the determined relative ToF. The processor 46 may further be configured to determine a relative amplitude or relative power at two of the plurality of subterranean antennas at different depths to estimate an attenuation coefficient, and estimate a soil electroconductivity based on the estimated attenuation coefficient and the estimated soil permittivity. In one embodiment, a machine learning model may be used to receive, as input, vectorized covariance matrices of channel state information (CSI) of the wireless signal, and output the estimated soil permittivity, as described in further detail below. As one example, a support vector machine executing a support vector regression model may be used as the machine learning model. Further, the machine learning model may be extended to compute the permittivity of a material other than soil into which the antenna is inserted. The processor may be further configured to estimate a soil moisture level based on the estimated soil permittivity and/or the estimated soil electroconductivity. However, in other embodiments, the processor 26 of the receiver 20 or a processor of another downstream computing device may be configured to determine the relative ToF and/or relative amplitude/relative power. The downstream computing device may be configured to output the estimated soil permittivity and/or the estimated soil electroconductivity via the display interface 49. The processor may be further configured to transmit the estimated soil permittivity and/or the estimated soil electroconductivity via a wireless or wired connection to a downstream computing device, which may be the same device that transmitted the wireless signal to the receiver device, or which may be a different device.

Accordingly, Wi-Fi transmissions in the unlicensed spectrum can be used to sense soil moisture and soil EC. System 10 may be implemented in the 2.4 GHz unlicensed bands over various hardware, including USRP, WARP, and a wireless network interface controller (NIC) such as Intel or Qualcomm Atheros based Wi-Fi cards, and system 10 has been demonstrated to perform as well as the more expensive soil sensors.

The wireless radio transmitter 44 and receiver device 20 of system 10 may each be selected from the group consisting of USRP, WARP, and wireless network interface controller (NIC) such as Intel Wi-Fi Link 5300 NIC and Atheros AR9590 Wi-Fi NIC to measure soil moisture and EC at 2.4 GHz, or other suitable frequency. In one example, a wireless NIC serving as the wireless radio transmitter 44 may be provided in a portable computing device, such as a smartphone. USRP may be configured to perform wideband experiments for ground truthing. The WARP board may be configured to replicate CSI measurements similar to Wi-Fi cards, and microbenchmark the performance of the system. The present inventors implemented the system on two off-the-shelf Wi-Fi cards to validate results.

USRP N200 devices with SBX daughterboards may operate on 400-4400 MHz, however, the transmission power of the SBX daughterboards drops as frequency increases. Therefore, measurements preferably use a bandwidth that spans from 400 MHz to 1400 MHz. One USRP device may be used as transmitter and the other as receiver. To emulate a multiple-input and multiple-output (MIMO) capable receiver equipped with multiple antennas, antennas may be switched during the measurements. For each antenna, the system sweeps through the 400-1400 MHz bandwidth with a step size of 5 MHz. To allow such an emulation, phase-locked loop (PLL) offsets, carrier frequency offset (CFO), sampling frequency offset (SFO), and packet detection delay (PDD) are preferably consistent for all the receiver antennas. Two features may be employed on USRP to eliminate PLL offsets, CFO and SFO; (i) SBX daughterboards have a PLL phase offset resync feature to synchronize PLL phase offsets on two USRPs after each frequency retune; (ii) Two devices can be connected with a MIMO cable to get time and frequency synchronization. To reduce the effect of PDD, a narrowband sinusoid may be used to estimate CSI.

WARP boards and the Wi-Fi cards are both MIMO capable and can operate on 2.4 GHz and 5 GHz. With these two types of devices, the transmitter and receiver may not share oscillators. Therefore, a key challenge is to extract CSI information from PLL offsets, CFO, SFO, and PDD corrupted CSI data. The Intel Wi-Fi cards have a well-known issue of random phase jumps at 2.4 GHz while WARP boards and the Atheros cards do not have such an issue. Since WARP has better support for manual configuration, especially gain settings, the performance of the system is preferably evaluated with WARP. A fixed transmit power of 8 dBm may be used, which is much lower than the FCC-imposed power limit for 2.4 GHz channels. The Wi-Fi cards may be set into monitor mode using the open-source CSI tools on Linux, for example.

The entire 70 MHz bandwidth at 2.4 GHz spectrum may be used to cope with potential multipath and amplitude variations that occur due to soil heterogeneity and antenna impedance change. To use the entire bandwidth, switching across the channels is performed. Therefore, there is a need to compensate for hardware impairments that lead to inconsistent measurements across channels. The calibration on WARP has two procedures. First, the PLL phase offsets are calibrated across channels by leveraging a key observation: although PLL phase offsets are different at different channels, they are constant after a frequency retune. Therefore, the PLL phase offsets at all the channels can be calibrated at the same time and do not need re-calibration unless nodes are reset. Then the phase sanitization algorithm is adopted in SpotFi to equalize the impact of PDD and SFO on channel phase slopes across multiple channel measurements. For Wi-Fi cards, since the RF chains share the same PLL, their random phase behavior is simpler than WARP, which only has two possible states separated by n.

Figure 5C:
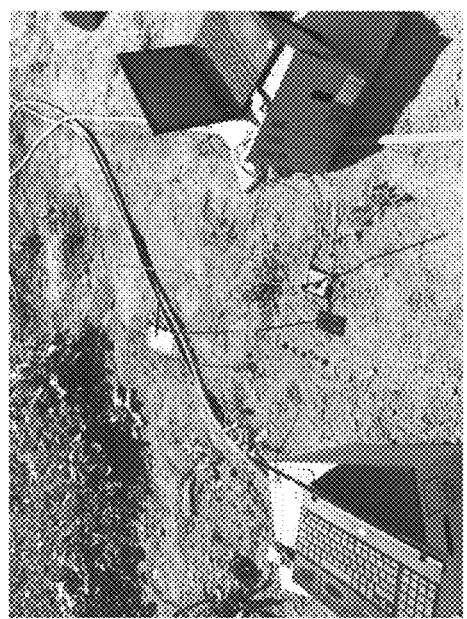
FIGS. 5A-5C illustrate an exemplary soil measurement setup for the soil measurement system according to one implementation of the present disclosure.
Figure 5B:
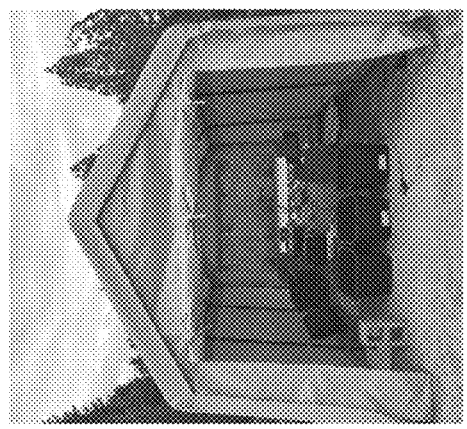
Figure 5A:
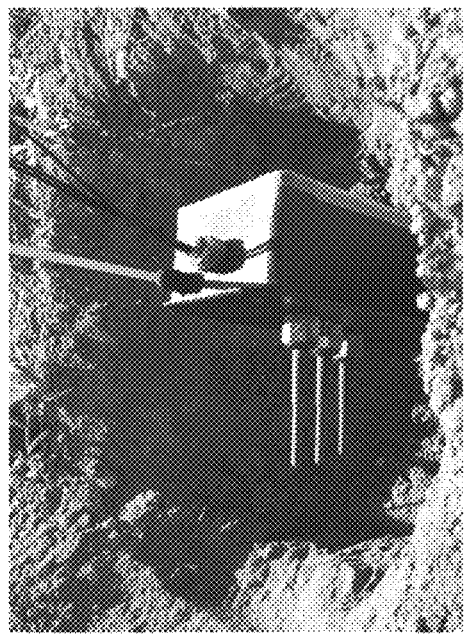

As depicted in FIG. 5A, a waterproof enclosure, such as a box, may be used to protect the connectors of antennas as well as hold antennas at different depths in soil, and there may be a rod protruding from soil surface to indicate to farmers where the antennas are buried. FIG. 5B illustrates soil boxes protected by a tent. FIG. 5C illustrates a soil measurement setup on a farm.

To conserve battery power, the receiver device 20 may be configured to enter a deep sleep mode, and "wake up" only when the soil surveying device 40 is nearby. The Network List Offload (NLO) feature of Wi-Fi may switch the receiver device 20 into a very low power mode until it receives a beacon with a predetermined Basic Service Set Identifier (BSSID) which is emitted by the soil surveying device 40. In other words, the soil surveying device 40 may be programmed to emit a wireless beacon frame with the predetermined BSSID to "wake up" the receiver device 20.

Antennas and RF chains on a MIMO capable Wi-Fi soil surveying device 40 are synchronized in time and frequency. Previous work has shown that such antennas can be utilized to estimate angle of arrival (AoA) based on path difference across antennas on an array. In air, this path difference, $\Delta l$, corresponds to a delay of $\Delta\tau = \Delta l/c$, where c is the speed of light.

One key insight here is that, if the path difference happens in soil, this delay will be longer due to slower wave velocity. Although permittivity can be calculated from $K_a = (c\tau/d)^2$, the difference is that the ToF $\tau$ in $K_a = (c\tau/d)^2$ is no longer the absolute ToF of a signal that travels from the transmit antenna to the receive antenna, but the ToF difference from between multiple receive antennas. It will be appreciated that relative ToF refers to the delay caused by the path difference between two adjacent antennas on the array. Unlike absolute ToF, the accuracy of relative ToF is dominated by the carrier frequency instead of bandwidth. Hence it is possible to get better resolution for relative ToF than absolute ToF.

The other key insight in the system is that the multiple antennas can be placed to create a path difference in soil, such that the relative ToF maps to permittivity, where the transmitter is in air and the receiver antenna array is in soil. The receive array may have three antennas, as is typical in commodity Wi-Fi devices. However, it will be appreciated that the number of antennas is not particularly limited, and the receive array may have two, four, or more antennas, for example.

Figure 2:
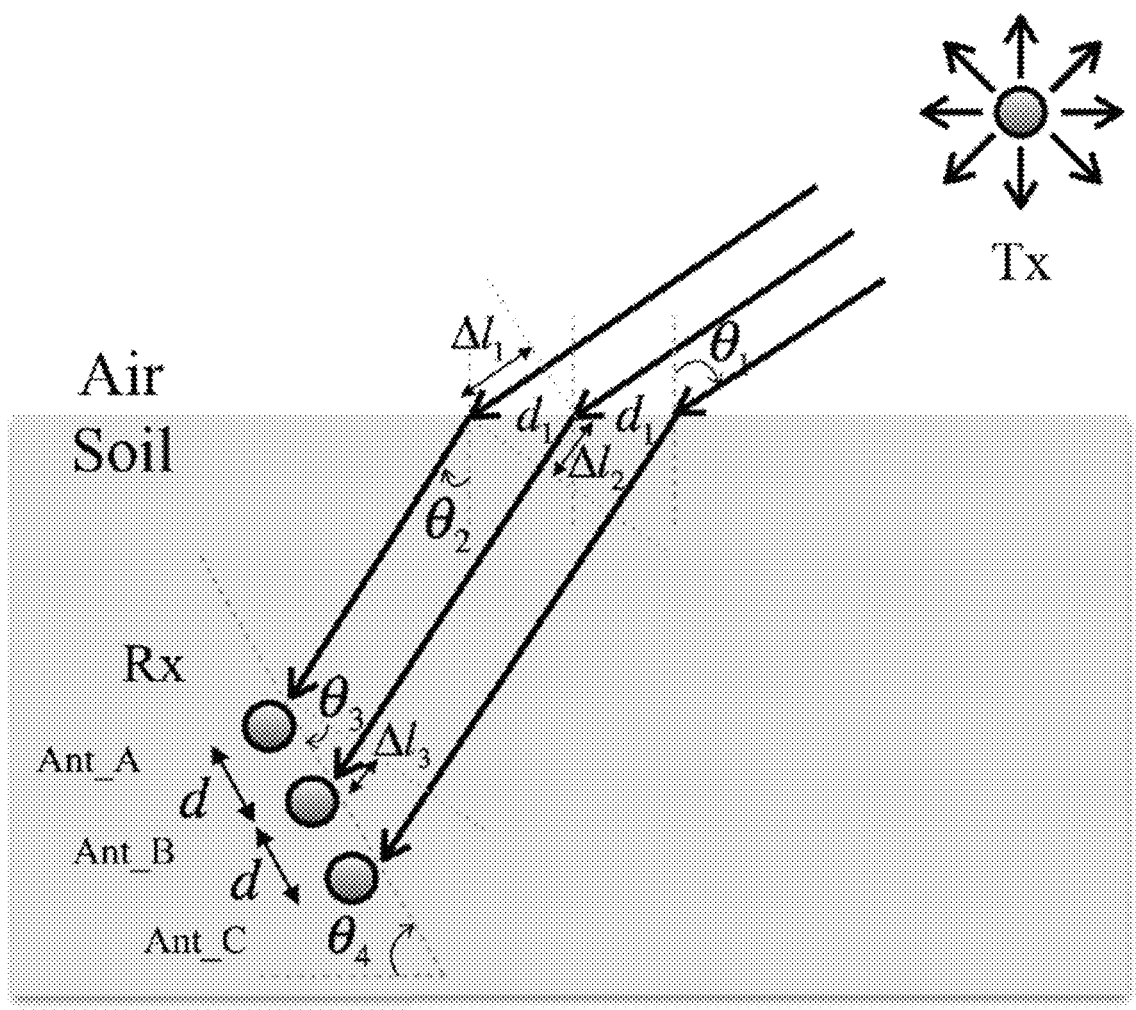
FIG. 2 schematically shows a model of a plane wave propagating through an air-to-soil surface.

FIG. 2 illustrates the relationship between relative ToF and path difference in soil using the air-to-soil wave propagation model. Transmit and receive antennas are oriented perpendicular to the plane of the paper. The wave travelling to antenna B has a delay of $n\Delta l_2/c + n\Delta l_3/c - \Delta l_1/c$ relative to the wave travelling to antenna A. Using the relative ToF estimation, soil permittivity may be estimated. For simplicity, the concept refractive index n is introduced to describe the slow down effect of soil, which relates to the permittivity as follows:

$$n = \sqrt{K_a} \qquad (14)$$

When signal travels from the transmitter to the receive antennas, the wave is refracted at the air-to-soil surface. Therefore, the path length difference of two adjacent antennas now consists of three parts: $\Delta l_1$, $\Delta l_2$, $\Delta l_3$. $\Delta l_1$ and $\Delta l_2$ are near the surface, while $\Delta l_3$ is near the antenna array. Since the speed of wave in soil is c/n, the additional time it takes to travel these path length differences, i.e., relative ToF, is $$\Delta\tau = \frac{\Delta l_1}{c} - \frac{n\Delta l_2}{c} + \frac{n\Delta l_3}{c} = \frac{\Delta l}{c} \qquad (15)$$

In Equation (15), $\Delta l = \Delta l_1 - n\Delta l_2 + n\Delta l_3$ is the equivalent total distance difference. It will be appreciated that $\Delta l$ contains information of soil refraction index, n. Next, $\Delta l$ is calculated to find out its relationship with n, and then soil permittivity $\varepsilon$. $\Delta l_1$, $\Delta l_2$, $\Delta l_3$ are given as $$\Delta l_1 = d_1 \sin\theta_1, \; \Delta l_2 = d_1 \sin\theta_2, \; \Delta l_3 = d \sin\theta_3 \qquad (16)$$

In Equation (16), d is the distance between antennas on the antenna array, $d_1$ is the distance between waves going to the antenna array at the air-to-soil surface, $\theta_1$ is the angle of incidence, $\theta_2$ is the angle of refraction, $\theta_3$ is the angle of incident wave at the antenna array.

The refraction at air-to-soil surface follows Snell's law, so $\theta_1$ and $\theta_2$ have the following relationship $$\sin\theta_1 = n \sin\theta_2 \qquad (17)$$

Therefore, $\Delta l_1 = n\Delta l_2$ so that $\Delta l = n\Delta l_3 = nd \sin\theta_3$. $\theta_3$ is a function of the angle of refraction and the angle of antenna array, $\theta_4$.

$$\theta_3 = \theta_4 - \theta_2 \qquad (18)$$

The $\Delta l$ may be rewritten as $$\Delta l = nd\sin(\theta_4 - \theta_2) = nd\sin\left(\theta_4 - \arcsin\left(\frac{\sin\theta_1}{n}\right)\right) \qquad (19)$$

In Equation (19), d and $\theta_4$ are parameters that can be controlled during the deployment of the antenna array, which are independent of soil moisture. $\theta_1$ depends on the location of transmit antenna and n. Note that in the case of normal incidence, $\theta_1$ is 0 and is independent of n. If $\Delta l$ or the corresponding relative ToF $\tau = \Delta l/c$ can be known, then n and $K_a$ can be estimated.

As discussed above, measuring EC from absolute RF amplitude measurements is prone to errors, and difficult to implement and calibrate. Instead, the present inventors developed a new technique that uses the ratio of amplitudes across multiple antennas, which will be called the relative amplitude, to estimate the EC. This avoids the need to calibrate several other parameters, such as antenna gains, impedance, etc.

When wave travels from air into soil, the signal power attenuation is modeled as follows:

$$\frac{P_t}{P_r} = T \frac{1}{G_t G_r} \left(\frac{4\pi(d_s\sqrt{K_a} + d_a)f}{c}\right)^2 e^{2\alpha d_s} \qquad (20)$$

In Equation (20), $d_s$ and $d_a$ are the distances the wave travels in soil and air, respectively. T is the transmission coefficient caused by the refraction at air-to-soil interface, which is a function of incident angle and soil permittivity. It will be noted that for three closely-located and orientation-aligned antennas, their values of T are similar. Furthermore, since soil moisture does not vary much within a small area, the three antennas experience similar impedance change and hence have similar receive gains $G_r$. $G_t$ is the same for the three antennas since they simultaneously receive the same packet from the same transmitter.

Therefore, instead of looking at the absolute amplitude, the difference between attenuation of two antennas at different depths, i.e., relative attenuation, is used:

$$\frac{P_r(d_{s1}, d_{a1})}{P_r(d_{s2}, d_{a2})} = \left(\frac{d_{s2}\sqrt{K_a} + d_{a2}}{d_{s21}\sqrt{K_a} + d_{a1}}\right)^2 e^{2\alpha(d_{s2} - d_{s1})} \qquad (21)$$

Comparing Equation (21) with Equation (20), the relative amplitude eliminates a lot of system parameters and is less vulnerable to the transmit antenna's location change. In the case of normal incident where $d_{a1} = d_{a2}$ and far field, the above equation can be reduced to $P_{rel}(\Delta d) = e^{2\alpha\Delta d}$.

Recall that in Equation (17), the large values of n in soil limit the angle of refraction to be small. This indicates that $d_{si}$ can be approximated to the depth of the $i^{th}$ antenna, which is known during the deployment of the receive antenna array. Therefore, the relative amplitude or relative power at two antennas at different depths can be used to estimate the attenuation coefficient and then figure out the EC value from Equation (3) or Equation (13).

To make a good estimation of soil moisture from the relative ToF, antenna array parameters that are included in (19) are carefully chosen. Specifically, these parameters are: (i) antenna distance, d, (ii) antenna array rotation $\theta_4$, and (iii) angle of incident wave, $\theta_1$. Additionally, a proper frequency band is chosen as the wave's carrier frequency.

The refractive index of soil, n, is usually a value between 2 and 6, which makes $\theta_2$ a small value (usually below 10 degrees) according to Snell's law. This implies that when the wave is incident on the soil surface, the incident point of the shortest path is usually around the area right above the receiver antennas. Given an antenna distance of d, the distance between the incident points of waves that go to different antennas is around d cos $\theta_4$.

Equations (14)-(19) are based on the assumption that soil is a homogeneous medium and the surface is totally flat. However, the real-world soil surface is often rough, and soil moisture can vary even within a small area. A depth variation of $\Delta d$ will lead to a ToF variation of $n\Delta d/c$. Consider $\Delta d=0.01$ m and n=3, the ToF variation is 0.1 ns. If a carrier frequency of 2.4 GHz is used, the phase difference caused by this variation is $0.48\pi$. To reduce the effect of soil non-homogeneity, d cos $\theta_4$ is preferably as small as possible, i.e., either d or cos $\theta_4$ is relatively small. In practice, d is preferably a relatively big value to tolerate variations caused by soil heterogeneity and reduce possible reflections from nearby antennas. Since $\theta_2$ is a small value in soil, setting $\theta_4$ to be 90 degrees is likely to cause blockage of the bottom two antennas' line-of-sight (LoS) paths. Therefore, $\theta_4$ is preferably a value around 90 degrees that does not cause blockage.

Figure 3:
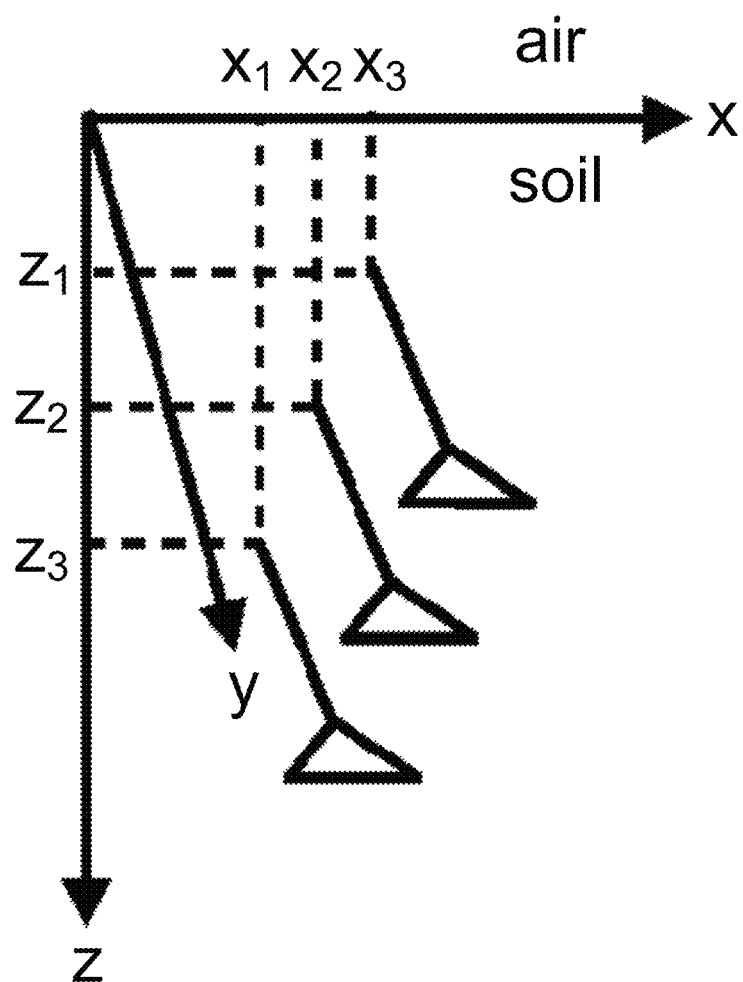
FIG. 3 is a schematic illustration of an antenna array setup in soil.

FIG. 3 shows a real-world example of an antenna setup in soil. Antenna distances in the x-axis are set to be the same so that $\Delta x = x_3 - x_2 = x_2 - x_1$. Three antennas are set at different depths, and the distance between two adjacent antennas in the horizontal plane is relatively small. Additionally, $\Delta x$ is set to be a small value to reduce the effect of soil non-homogeneity. Antenna distances in the z-axis are also set to be the same so that $\Delta z = z_3 - z_2$ $z_2 - z_1$. The depth difference, $\Delta z$, is set to be a relatively large value to tolerate possible variations in soil structure.

As shown in Equation (20), signal attenuation in soil is frequency-dependent. Higher frequency signals have higher attenuation. Therefore, a frequency that can at least penetrate to the bottom antenna is preferably chosen.

Figure 4A:
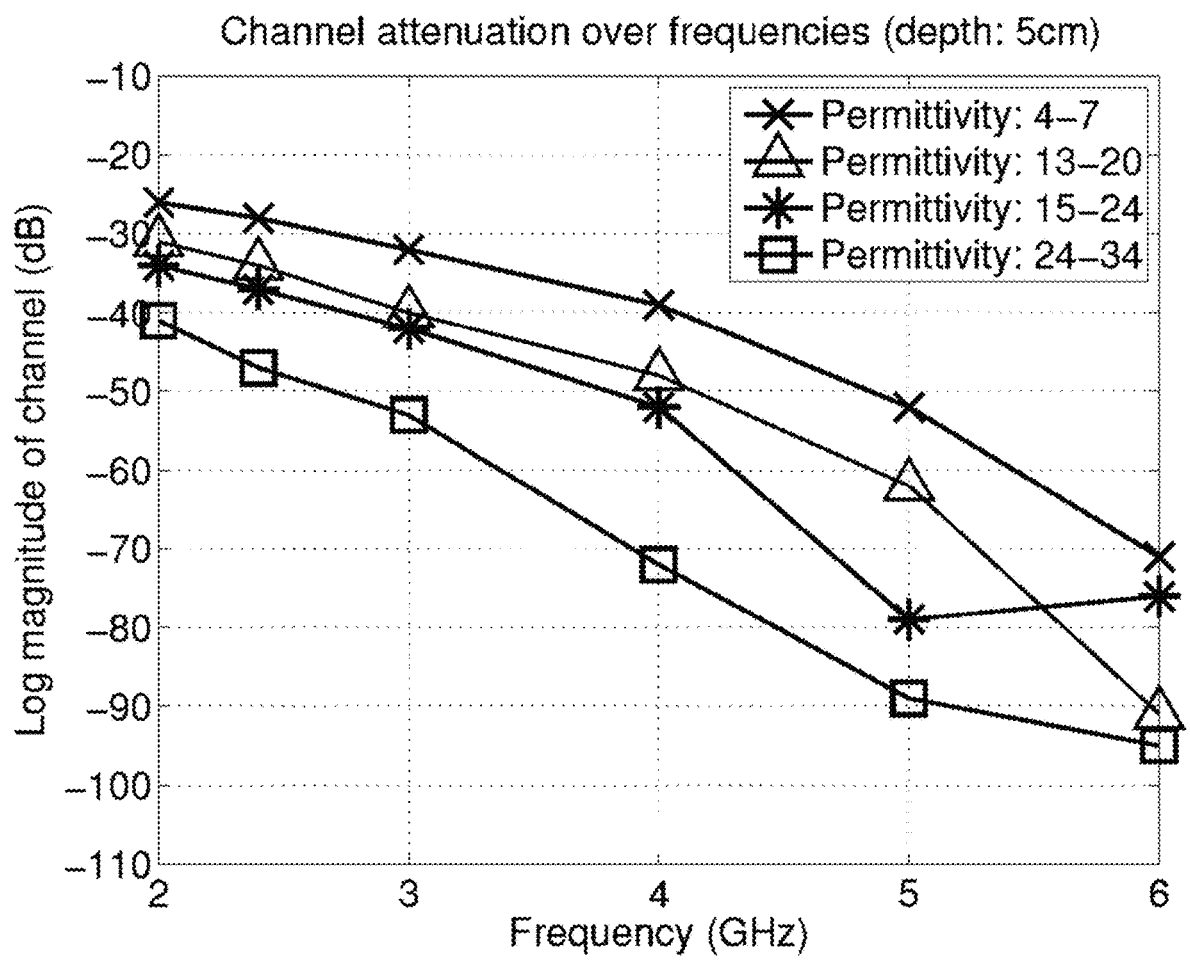
FIGS. 4A-4C plot the signal attenuation in soil for the three receive antennas at three different depths as measured by a network analyzer.
Figure 4B:
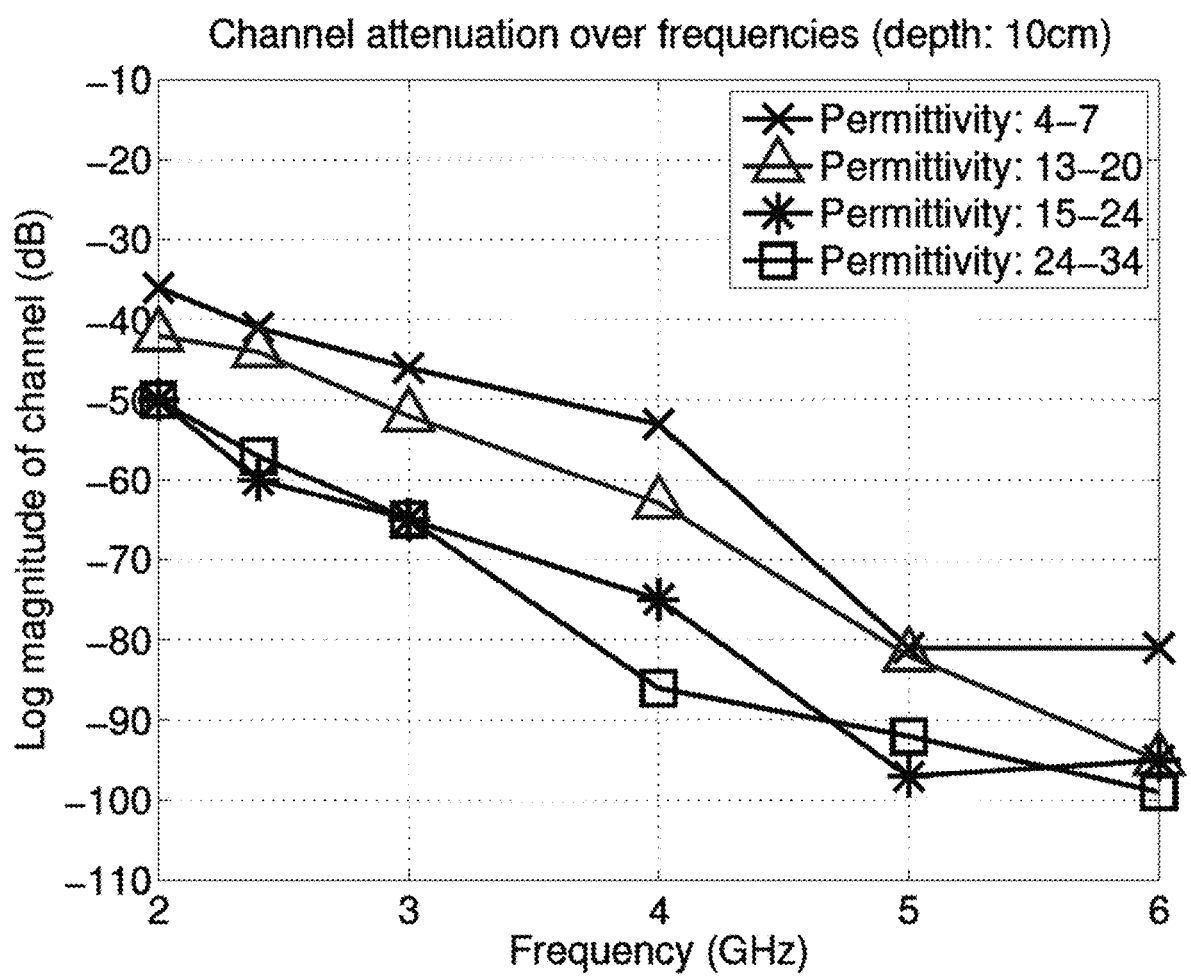
Figure 4C:
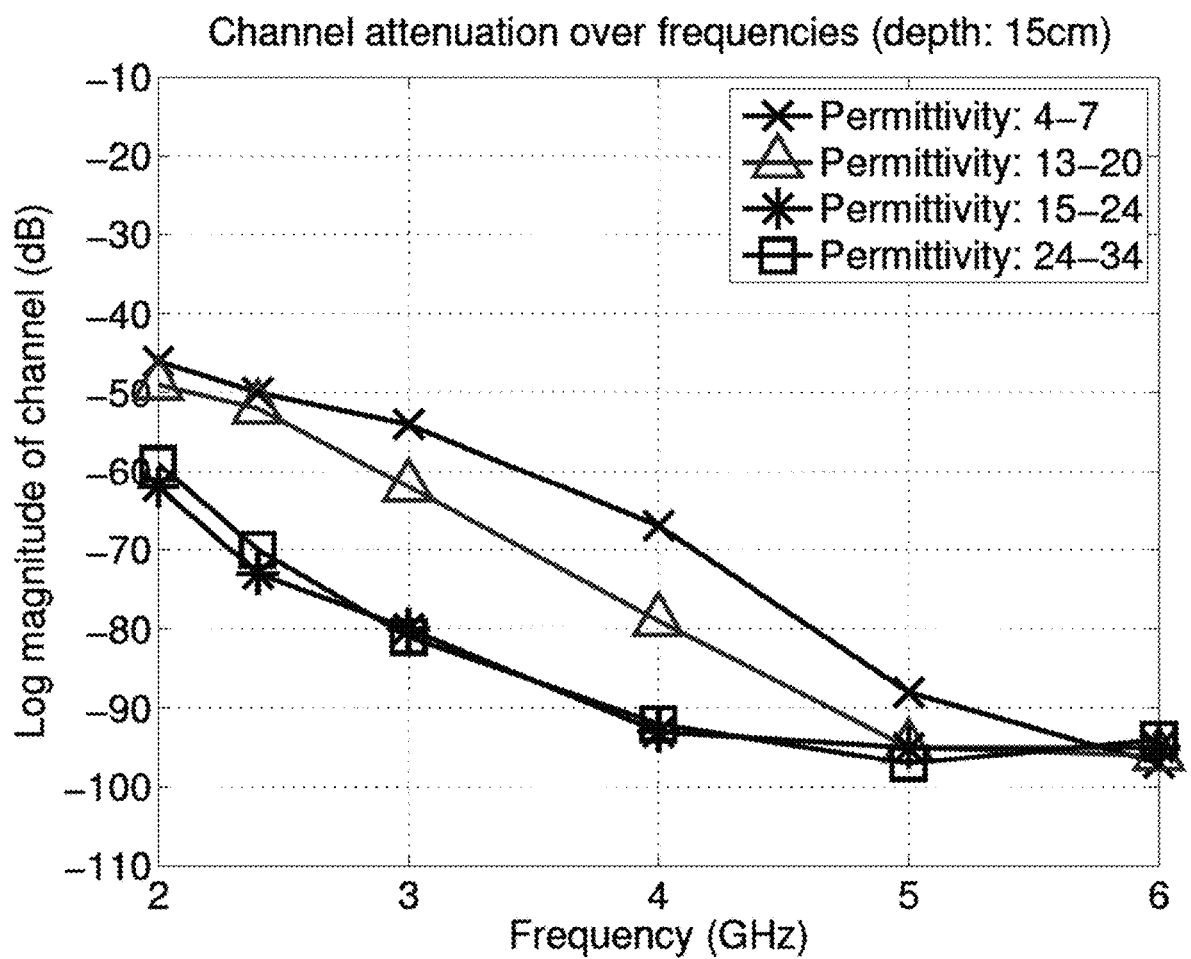

To understand how Wi-Fi frequency bands perform in soil at different moisture levels, the present inventors conducted measurements with a network analyzer in potting soil. Since frequency below 1 GHz is known to have good performance in GPR applications, here the main focus is to look at signal attenuation at Wi-Fi frequency bands, i.e., 2.4 GHz and 5 GHz. FIGS. 4A-C plot the signal attenuation in soil for the three receive antennas at depths of 5 cm, 10 cm and 15 cm in soil. In FIGS. 4A-C, it will be appreciated that, generally, signal attenuation increases as frequency, depth, or soil moisture increases. With a transmission power of 15 dBm, the channels measured with smaller than −90 dB log magnitude do not contain useful phase information. It will be appreciated that the attenuation at 2.4 GHz channels maintain larger than −80 dB log magnitude at all moisture levels while 5 GHz channels do not have good signal strength for the bottom antenna even when the soil is very dry. Therefore, although 5 GHz channels have a total bandwidth span of about 665 MHz, the attenuation problem makes most of the data measured at 5 GHz invalid. These results indicate that it may be preferable to focus on using 2.4 GHz channels, which have about 70 MHz of available bandwidth.

Equations (14)-(19) only consider the shortest path from the transmit to the receive antennas. In practice, channels always consist of multiple paths. In the measurement setup used by the present inventors, the shortest path is also the strongest path in most cases. Therefore, the Multiple Signal Classification (MUSIC) algorithm was used to accurately recover the shortest path from a multipath channel.

In multipath environment, the CSI of $m^{th}$ antenna and $n^{th}$ frequency can be written as the sum of L paths $$h_{m,n} = \Sigma_{l=1}^{L} \alpha_{l,m} e^{-j2\pi(f_0 + \Delta fn)\tau_{l,m}} \quad (22)$$

In Equation (22), $a_{l,m}$ is the complex amplitude of $l^{th}$ path, $\tau_l$ is the absolute ToF of $l^{th}$ path and $\Delta f$ is the frequency spacing between two adjacent frequency samples.

If there is no time and frequency synchronization between the transmitter and the receiver, the measured CSI is corrupted with PDD, SFO, and CFO introduced by hardware, so the CSI becomes $$\hat{h}_{m,n} = \Sigma_{l=1}^{L} \alpha_{l,m} e^{-j\theta_0} e^{-j2\pi(f_0 + \Delta fn)(\tau_{l,m} + \tau_0)} \quad (23)$$

In Equation (23), $\theta_0$ is the phase shift caused by CFO and $\tau_0$ is the ToF shift caused by PDD, SFO, and other possible delays in hardware. $\theta_0$ and $\tau_0$ are the same across all the paths, subcarriers in a single channel, and antennas when the samples are measured at the same time.

Note that although $\tau_0$ is unknown, the relative ToF between two antennas can be obtained, $\tau_{l,i} - \tau_{l,j} = (\tau_{l,i} + \tau_0) - (\tau_{l,j} + \tau_0)$. For a uniform linear antenna array, the path difference remains the same for all adjacent antenna pairs under far-field assumption so that the relative ToF also remains the same, i.e., $\Delta\tau_l = \tau_{l,i} - \tau_{l,i+1} = \tau_{l,i+1} - \tau_{l,i+2}$. Therefore, the MUSIC algorithm can be used to jointly estimate absolute ToF ($\tau_{l,m} - \tau_0$) and relative ToF ($\tau_{l,i} - \tau_{l,j}$) in a similar way as Spotfi did. Here the absolute ToF refers to the total ToF consisting of PDD, SFO, and delays in hardware. However, Spotfi assumes the phase difference caused by the additional path difference is the same for all subcarriers, which requires $2\pi B\Delta\tau$ to be a small value, where B is the total bandwidth of N subcarriers. This is not true in the soil measurement system since a larger bandwidth is used to look at a longer relative ToF. Considering an antenna array with 3 antennas, a modified smoothed CSI matrix is constructed without smoothing CSIs of different antennas as follows:

$$\begin{bmatrix} h_{1,1} & h_{1,2} & h_{1,3} & \cdots & h_{1,K} \\ \vdots & \vdots & \vdots & \ddots & \vdots \\ h_{1,N-K+1} & h_{1,N-K+2} & h_{1,N-K+3} & \cdots & h_{1,N} \\ h_{2,1} & h_{2,2} & h_{2,3} & \cdots & h_{2,K} \\ \vdots & \vdots & \vdots & \ddots & \vdots \\ h_{2,N-K+1} & h_{2,N-K+2} & h_{2,N-K+3} & \cdots & h_{2,N} \\ h_{3,1} & h_{3,2} & h_{3,3} & \cdots & h_{3,K} \\ \vdots & \vdots & \vdots & \ddots & \vdots \\ h_{3,N-K+1} & h_{3,N-K+2} & h_{3,N-K+3} & \cdots & h_{3,N} \end{bmatrix} \quad (24)$$

The reason for the ambiguity issue is explained as follows, and then the method to remove it is discussed below. When a wave propagates at a carrier frequency of f, its phase variation is given by $$\theta = -2\pi f \tau \quad (25)$$

In Equation (25), t is the ToF. The time it takes the phase to rotate $2\pi$ is $\tau_0 = 1/f$. Assuming that the relative ToF of antennas at different depths is $\Delta\tau$, the phase of the three receive antennas at three depths are derived as: $\theta_1=-2\pi f\tau$, $\theta_2=-2\pi f(\tau+\Delta\tau)$ and $\theta_3=-2\pi f(\tau+2\Delta\tau)$. Due to phase ambiguity, the phase of the three receive antennas at the three depths are:

$$\theta_1 = -2\pi f \tau \qquad (26)$$
$$\theta_2 = -2\pi f(\tau + \Delta\tau) =$$
$$\qquad -2\pi f(\tau + (\Delta\tau + \tau_0)) = -2\pi f(\tau + (\Delta\tau + 2\tau_0)) = \ldots$$
$$\theta_3 = -2\pi f(\tau + 2\Delta\tau) = -2\pi f(\tau + 2(\Delta\tau + \tau_0)) =$$
$$\qquad -2\pi f(\tau + 2(\Delta\tau + 2\tau_0)) = \ldots$$

From the Equation (26), it will be appreciated that a delay of $\Delta\tau$ is equivalent to $\Delta\tau+\tau_0$, $\Delta\tau+2\tau_0$, .... Thus an infinite number of possible relative ToF values can be obtained with a separation of $\tau_0$. In 2.4 GHz channels, $\tau_0$ is about 0.4 ns.

Although the resolution of ToF-based method is theoretically limited by bandwidth, a question to ask here is: given a bandwidth, is the ToF estimation resolution the same as soil moisture estimation resolution? The answer is no, since the ToF information is not the only information that can be obtained from the received signal data. With commodity devices, it is possible to access signal strength and phase information from CSI, receive signal strength indicator (RSSI), and gain information. For example, the INTEL Wi-Fi Link 5300 chips have a software to extract CSI information together with other detailed information in the measurements including RSSI and automatic gain control (AGC) values. A key insight is that the lost information in the ToF-only methods can be helpful to reduce the requirement of bandwidth while achieving the same level of soil moisture estimation accuracy. Especially, the signal strength attenuation in soil is much stronger than in air and increases significantly as soil moisture increases. Other information such as antenna impedance change at different moisture levels may also be useful information.

To utilize all available information, a machine learning model such as a support vector regression (SVR) model may be used for soil moisture estimation. This model uses an error bound to give generalized results, which is perfect to efficiently deal with uncertainties in soil data. Additionally, SVR is a powerful technique that takes care of both linear and non-linear relationships of variables, which may help to discover non-linear properties hidden in CSI data. The inputs to the model are the vectorized covariance matrices of CSI given as $$r=[h_1h^*_1, \ldots, h_1h^*_n, h_2h^*_1, \ldots, h_2h^*_n, \ldots, h_nh^*_1, \ldots, h_nh^*_n]^T \qquad (27)$$

In Equation (27), $h_1, \ldots, h_n$ denote the CSIs measured at n frequencies within a certain bandwidth. The input matrix choice is based on the fact that the CSI covariance matrix is also the input of traditional signal processing methods such as MUSIC. The output is soil permittivity values. The SVR model was also tested with electrical conductivity and temperature and compared with data from the soil moisture sensor. This technique profiles the system (similar to other surrogate measurement techniques) for different soil types, and different moisture levels. This profiling phase is used to train the machine learning model for different soil types. In the field, the appropriate model is applied based on the soil type, for example, as indicated in the USDA National Resources Conservation Service (NRCS) database.

Next, it will be shown how the system leverages the knowledge of soil properties to remove this ambiguity. First, the refraction index in soil is known to be usually between 2 and 6. Therefore, when the antenna is set at a depth distance at a known value, e.g., 4.5 cm, it is known that the relative ToF range is 0.3-0.9 ns. In 2.4 GHz, if the relative ToF falls in 0.3-0.5 ns or 0.7-0.9 ns, ambiguity occurs. As explained in reference to FIGS. 4A-C, there is a large channel attenuation gap between the two permittivity ranges corresponding to the two ambiguity values. Although multipath and the rotation of transmit antenna may affect the signal strength, the signal strength of the three antennas and the data collected at different transmit antenna locations may be used to make a correct choice of antenna pairs to use for relative ToF.

The present invention will be described in more detail below by showing experimental results. The scope of the present invention is not limited to the experimentation described below as long as it does not depart from the scope of the present invention. In the experimental results below, the accuracy of the system was demonstrated in measuring relative ToF, and the performance of the system was evaluated in measuring soil permittivity, EC, and moisture. The present inventors used wideband USRP to measure ground truth, used Wi-Fi based measurements on WARP to microbenchmark the system, and also used Intel and Atheros Wi-Fi cards. Potting soil boxes were set up in a tent to conduct measurements with controlled salinity and moisture levels, and test real soils in outdoor environments.

The system is able to accurately estimate soil moisture and EC with limited bandwidth in 2.4 GHz Wi-Fi. Here, it is shown that with a few antennas at the receiver, the relative ToF estimation is very accurate even with a very small bandwidth. USRP was first used over a large bandwidth to micro-benchmark, and then WARP was used to evaluate the performance at 2.4 GHz channels.

Soil is not a homogeneous medium, and its variations can introduce shifts in estimated ToF. Therefore, the present inventors used over the air measurements to evaluate the system's performance in estimating absolute ToF. The ground truth ToF is the distance of antennas measured by tape measure and divided by speed of light. Measurements were conducted with USRPs by varying the distance between adjacent receive antennas from 0.1 m to 0.5 m. The distance between the transmit antenna and the receive antenna closest to it is 1.2 m and remains the same across all the measurements.

Figure 6A:
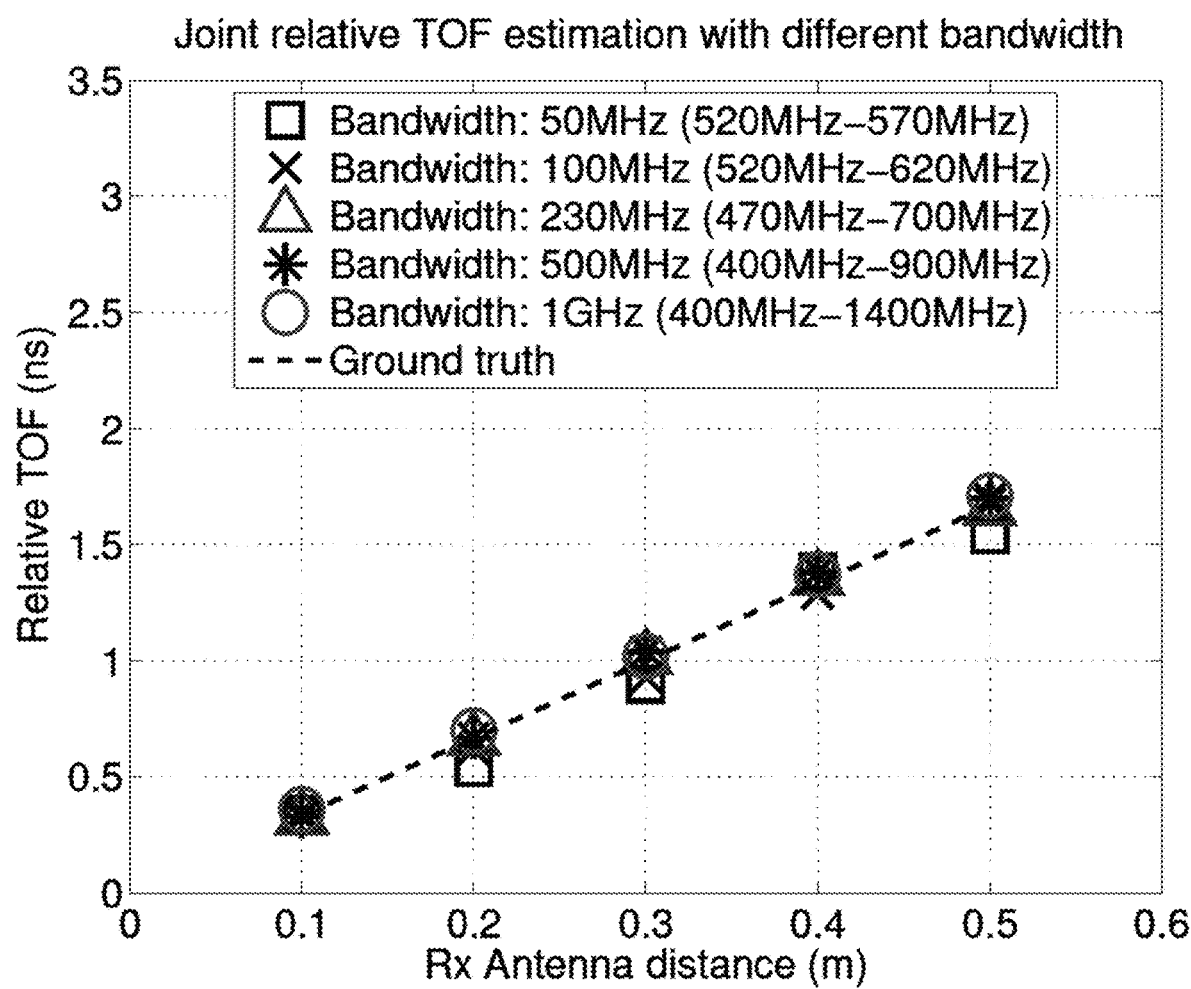
FIGS. 6A-6C plot the relative time of flight (ToF) and absolute ToF estimation results given by the joint estimation method and the separate estimation method.
Figure 6B:
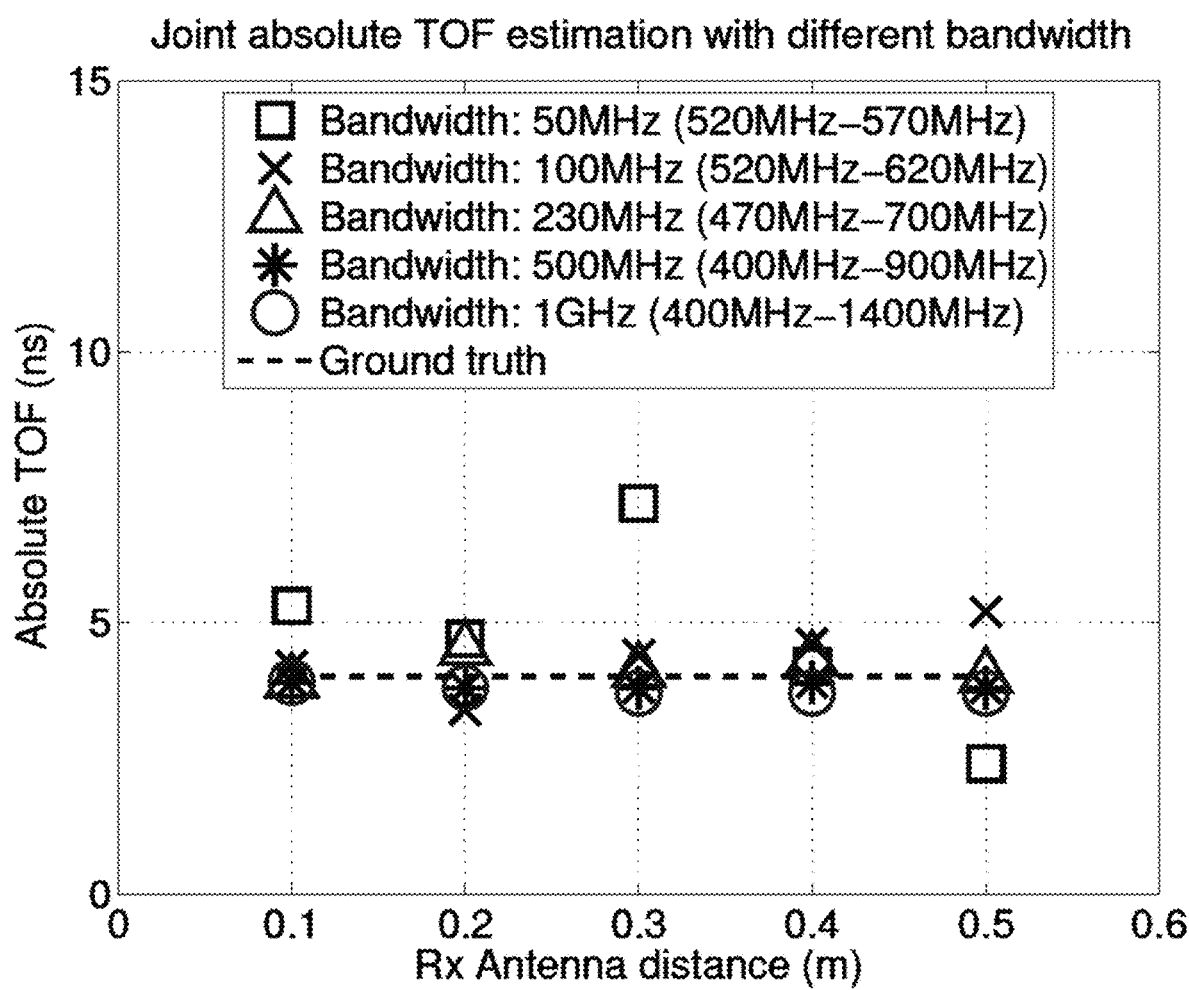
Figure 6C:
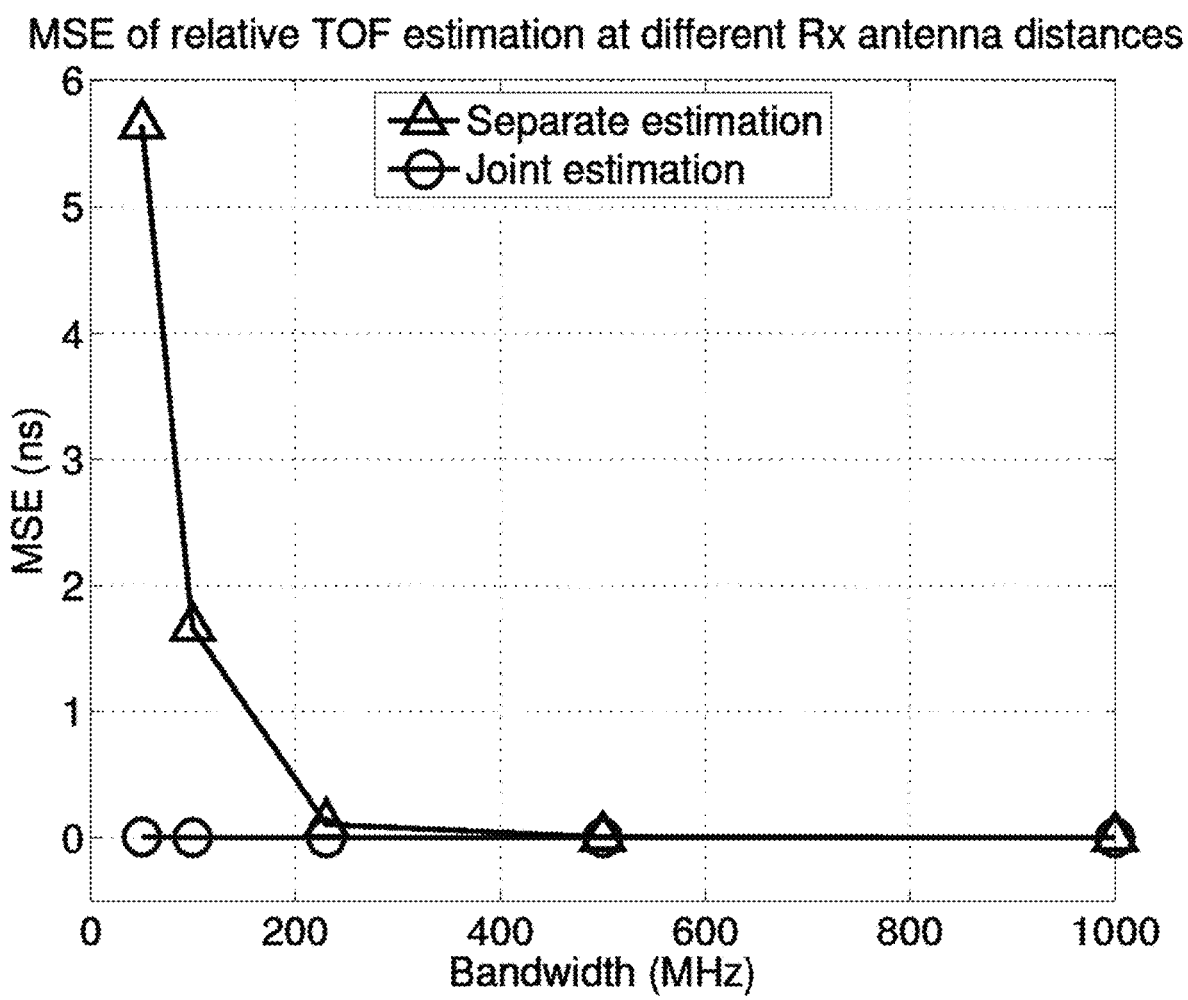

FIGS. 6A-C plot the relative ToF and absolute ToF estimation results given by the joint estimation method and the separate estimation method. FIG. 6A plots the joint relative ToF estimation results using three antennas to jointly estimate relative ToF and absolute ToF. FIG. 6B plots the joint absolute ToF estimation results for the antenna closest to the transmit antenna. FIG. 6C plots the mean squared error (MSE) of relative ToF estimation with different bandwidths. Relative ToF refers to the ToF difference between two adjacent antennas. The separate estimation method refers to first estimating absolute ToFs at the three antennas separately from the CSI collected by the three receive antennas and then calculating the relative ToF from the average difference of absolute ToFs. The joint estimation method estimates relative ToF and absolute ToF at the same time for the three antennas. Surprisingly, with the joint estimation method, even a relatively small bandwidth of 50 MHz gives accurate relative ToF results, although its absolute ToF estimation can deviate more from the ground truth. Furthermore, the joint estimation method has a much smaller MSE of relative ToF and absolute ToF estimation than the separate estimation with small bandwidth.

Here, the relative ToF estimation performance of the multi-antenna system in soil was examined. The experiments were conducted in potting soil in indoor environment. In the USRP experiments, the transmit antenna is set at a height of 1.08 m above soil surface, the receive antennas are put at different depths in soil. In the WARP experiments, the transmit antenna is 0.36 m above soil surface. The results were compared with the permittivity measured by a Decagon GS3 soil sensor, which can simultaneous measure permittivity, EC and temperature. In each experiment, the soil sensor was used to measure moisture at more than 10 locations in the area around the antenna array to account for heterogeneity of soil.

Figure 7A:
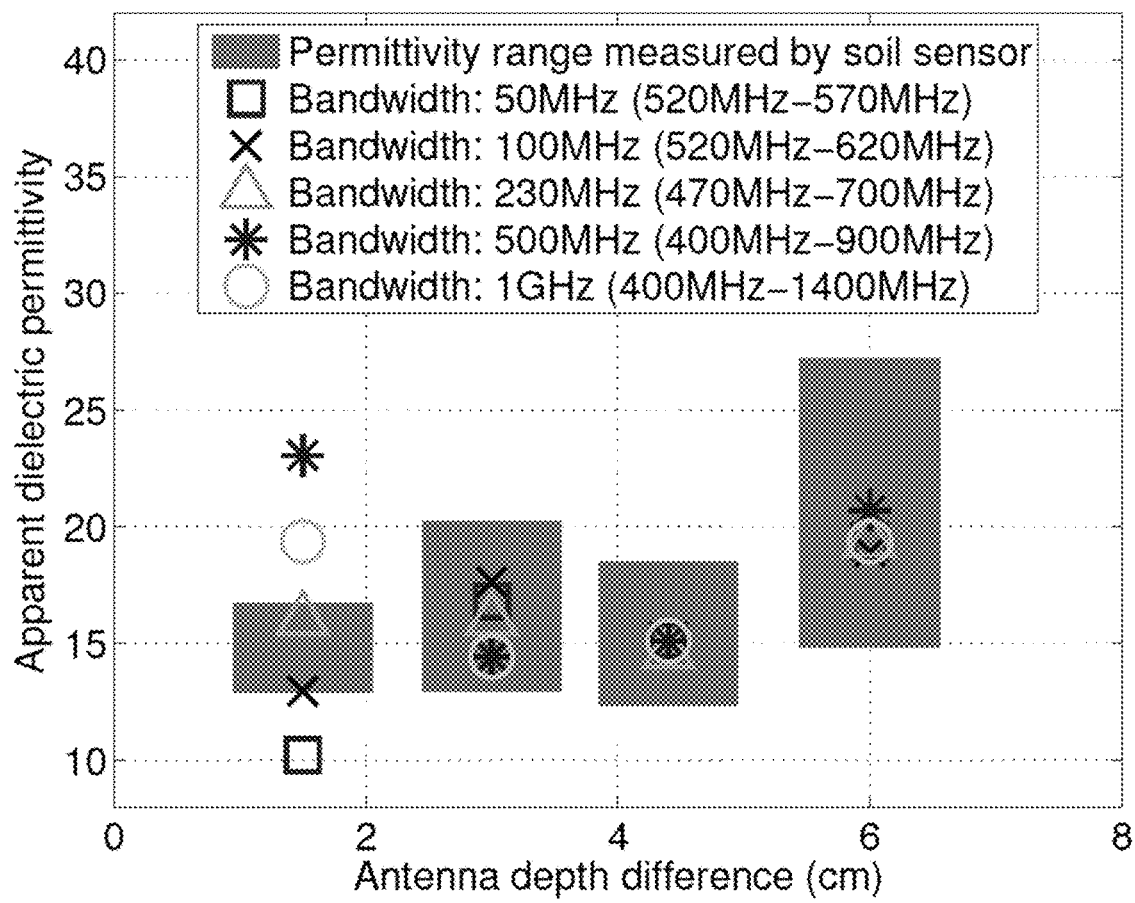
FIGS. 7A-7C plot the soil dielectric permittivity estimation results based on relative ToF.

The choice of antenna depth separation is the key factor that affects the relative ToF estimation accuracy in the antenna array design. Experiments were conducted with USRPs to examine the impact of depth difference. FIG. 7A plots soil permittivity estimation results based on relative TOF from USRPs with different antenna depth differences. Sensor data shows that soil moisture can vary within a certain range in an area. With a depth separation of 1.5 cm, the estimated permittivity can deviate a lot from the sensor data. The reason is that the depth separation of 1.5 cm is relatively small compared to possible path length variations that exist in the soil due to the heterogeneous nature of soil. With larger antenna depth separation, the permittivity values estimated by different bandwidth are more converged. Based on the results shown in FIG. 7A, an antenna depth separation of 4.5 cm was chosen to evaluate the performance of USRP and WARP.

Figure 7B:
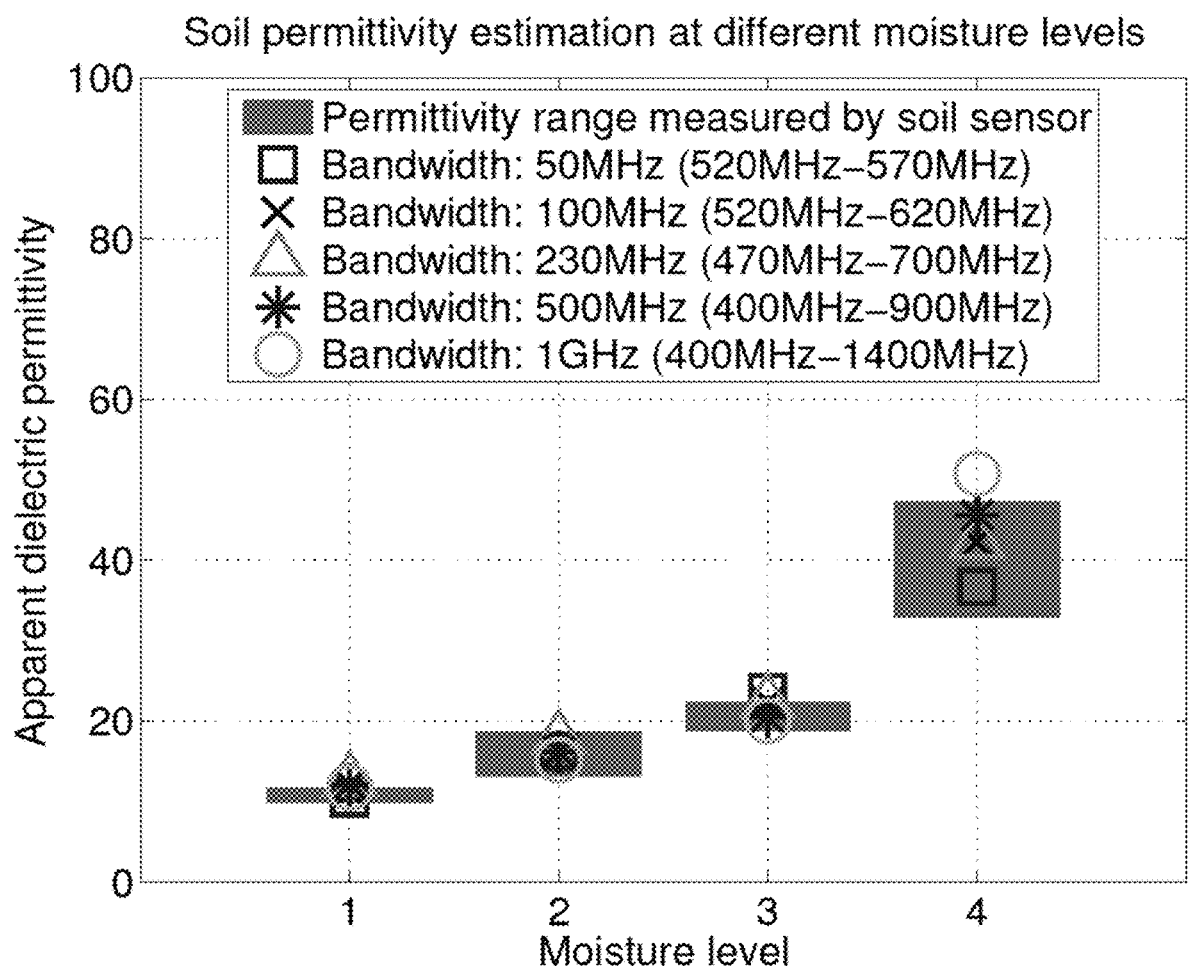

The soil moisture was varied by adding water, and the accuracy of the system was measured in determining different soil moisture levels. In each trial, the soil was stirred thoroughly to mix water into soil before burying the antenna array. FIG. 7B plots soil permittivity estimation results from USRPs at different moisture levels and with different bandwidths. The estimated ToF does not deviate too much from sensor data at all moisture levels even with a small bandwidth. It will be appreciated that the results at the highest moisture level diverge more than the others. This is because larger soil permittivity causes more attenuation of received signal strength, so that the CSIs are less accurate due to low SNRs.

Figure 7C:
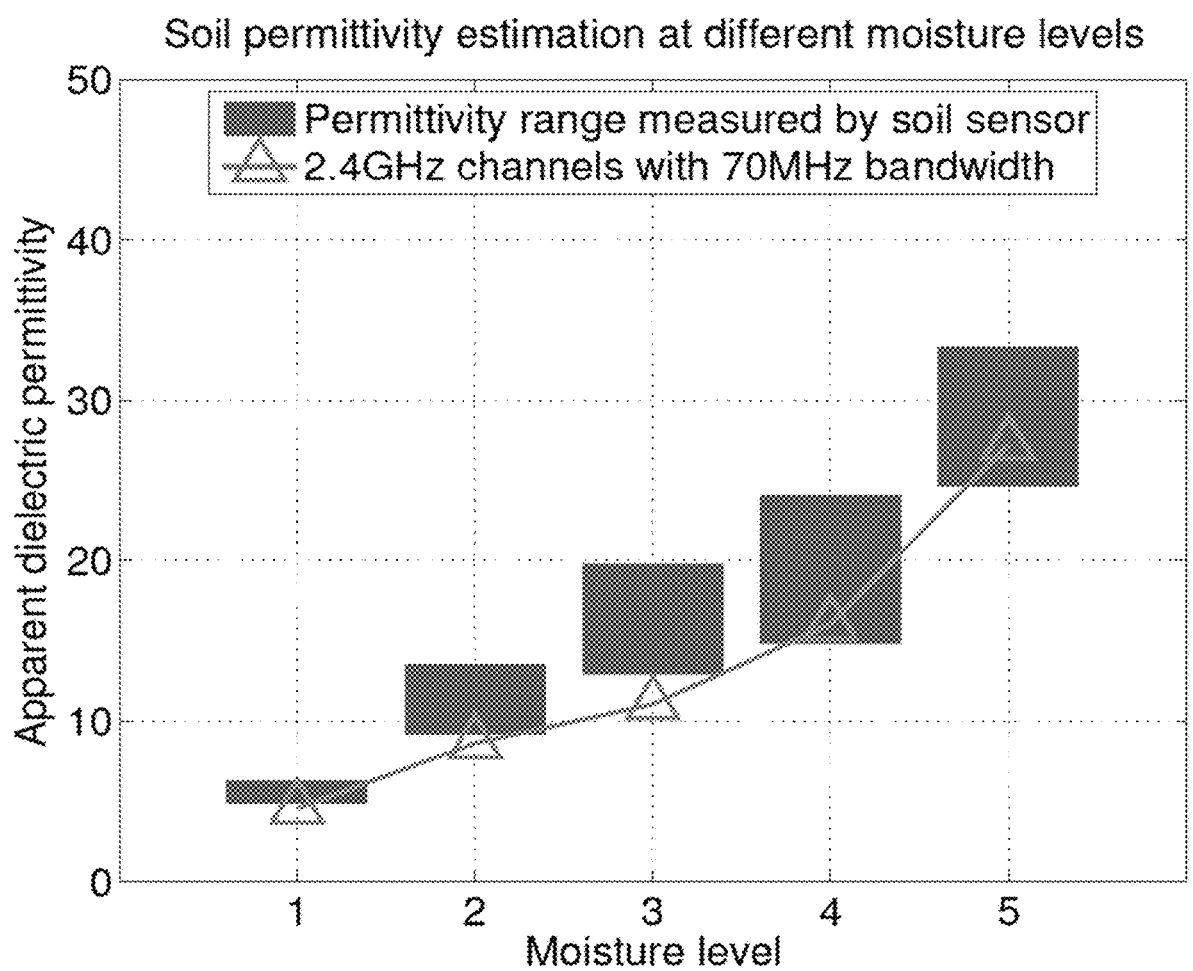

FIG. 7C plots soil permittivity estimation results from WARPs at different moisture levels, showing the estimated permittivity at 2.4 GHz measured by WARP with a bandwidth of 70 MHz. Estimated permittivity increases as moisture level increases. However, the estimated permittivity values are slightly smaller than sensor measurements. This is because of the frequency dependence of soil permittivity. This variation will be discussed later.

The performance of the system was then evaluated in estimating EC. Since EC estimation method in the system requires an initial estimation of permittivity, here the present inventors looked at the overall performance including both EC and permittivity. Since controlling EC of soil was non-trivial, the performance of the soil measurement system was measured at different salinity levels of soil, for different soil types. The three types of soils are shown in FIGS. 8A-C. Experiments were conducted in potting soil (illustrated in FIG. 8A) with three different salinity levels. The performance of the system was evaluated in two types of real soil: sandy loam (illustrated in FIG. 8B) and silt loam (illustrated in FIG. 8C). The sandy loam soil was located in a landscaping area near office buildings and the silt load soil was in a real farm.

Figure 9A:
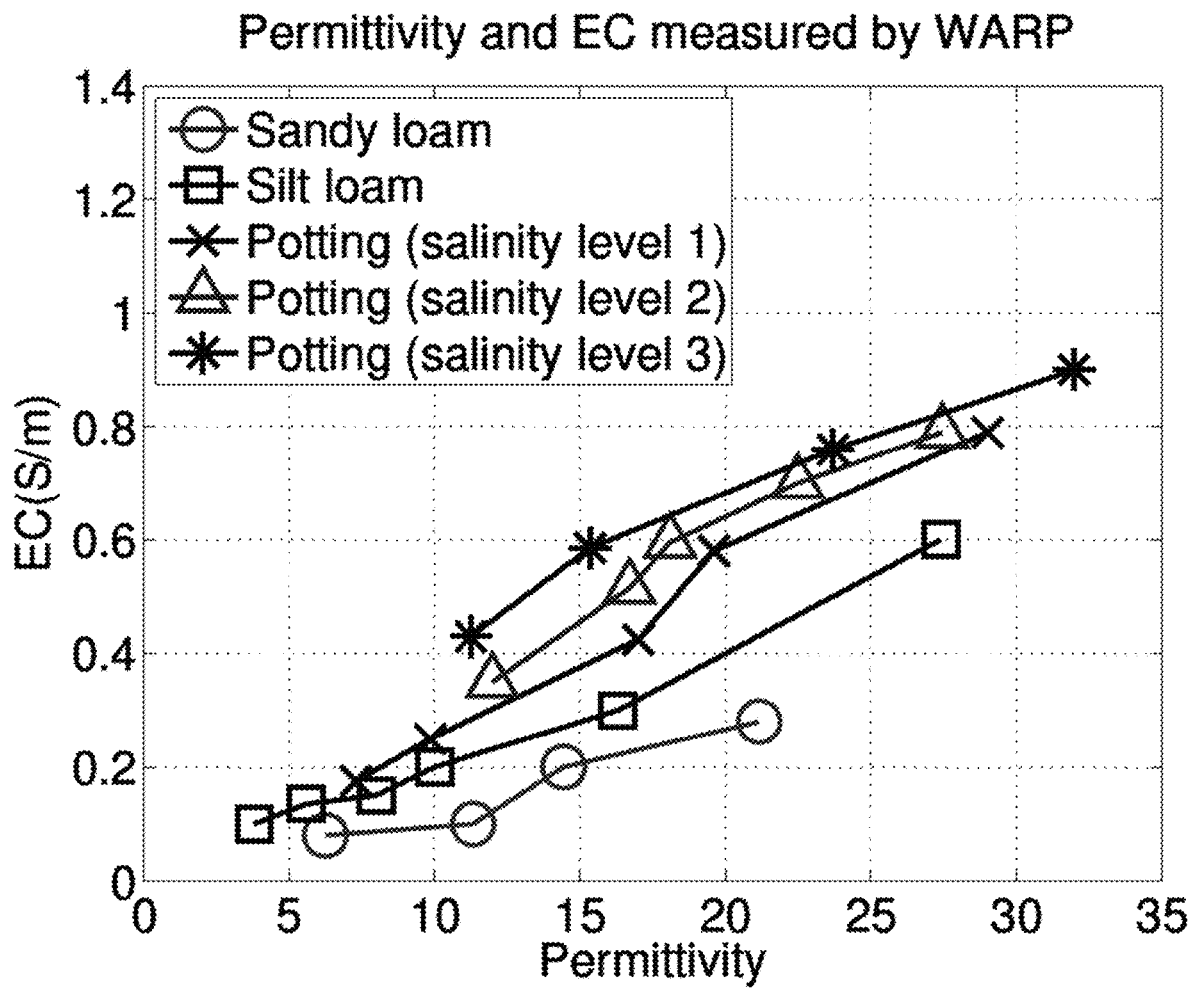
FIGS. 9A-9D plot different soil permittivity and EC estimation results for different soil types and salinity levels.
Figure 9B:
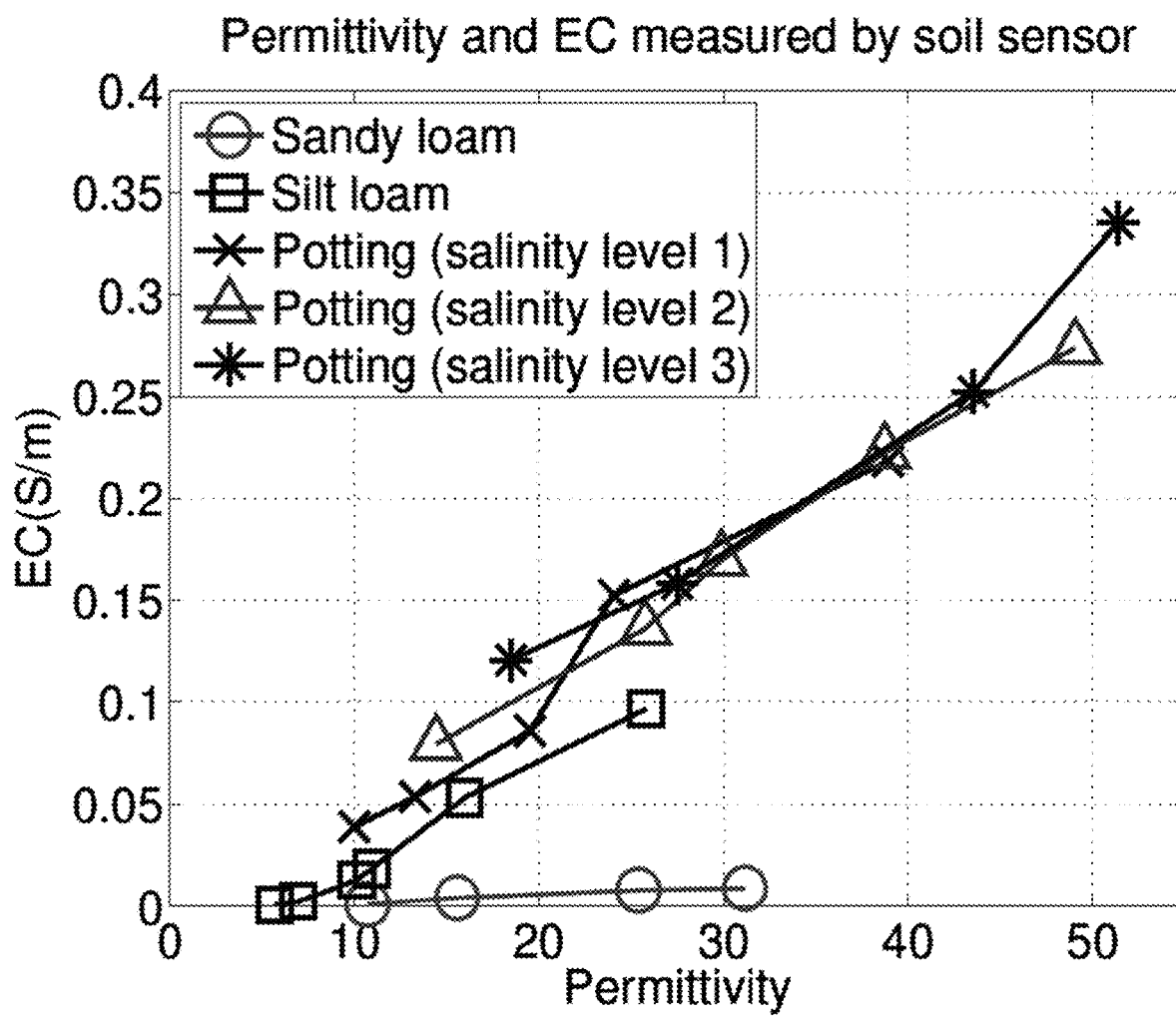
Figure 9C:
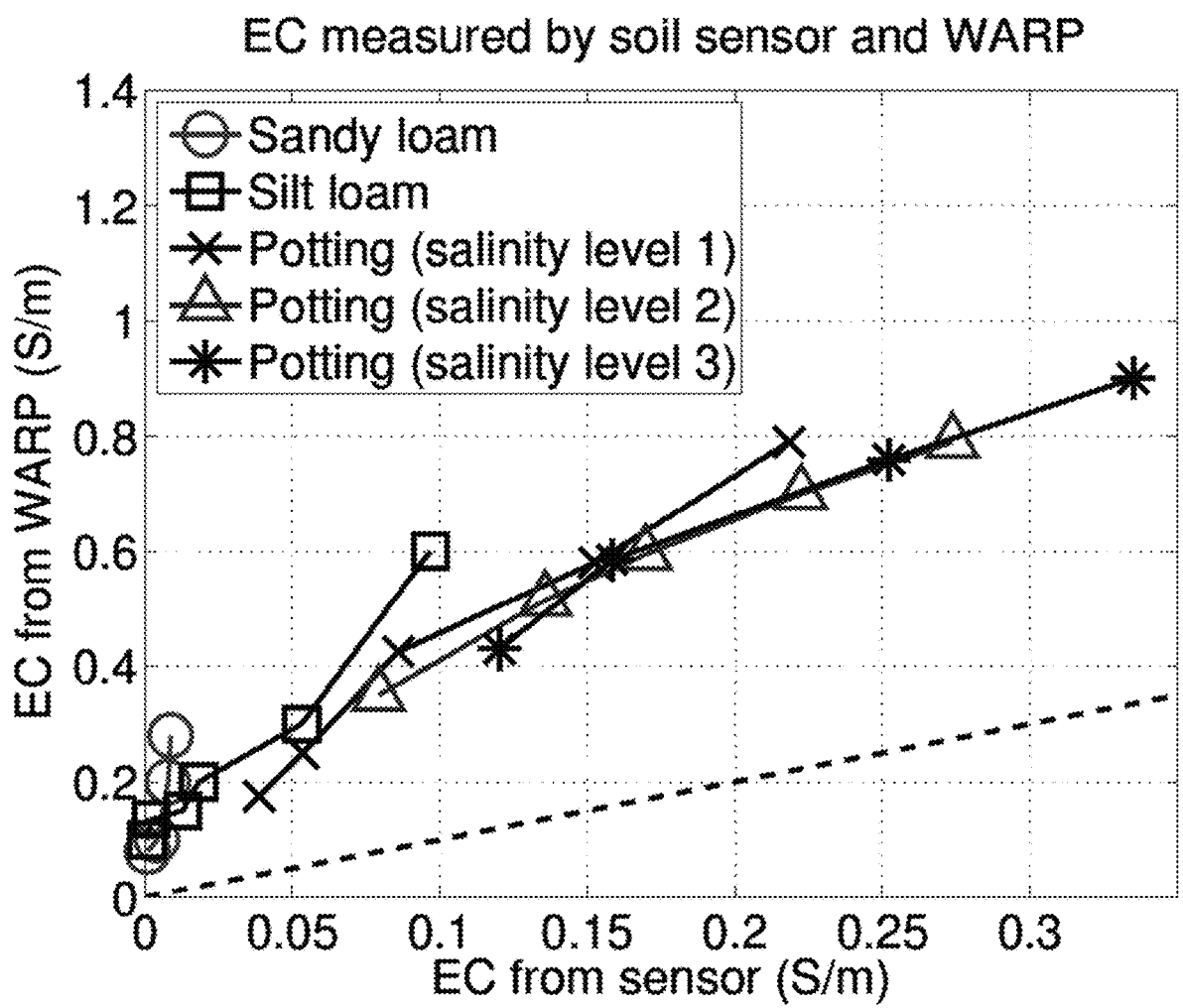
Figure 9D:
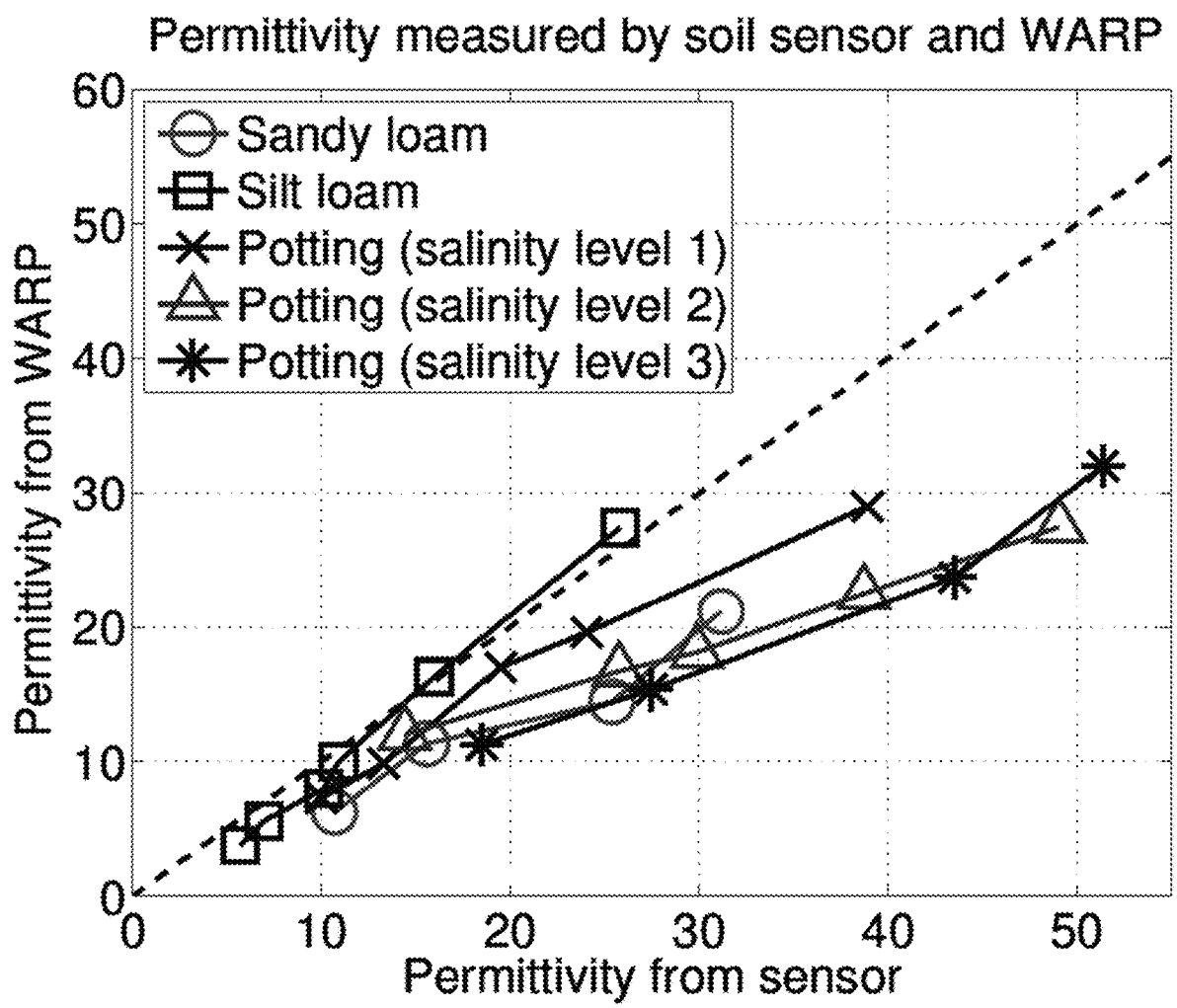

Referring to FIGS. 9A-D, soil permittivity and EC were estimated for different soil types and salinity levels. FIG. 9A plots soil permittivity and EC estimation results as measured by WARP with 2.4 GHz channels, showing that soil EC increases as the salinity level increases. FIG. 9B plots soil permittivity and EC estimation results as measured by a soil sensor at 70 MHz, where the permittivity estimation accuracy of the soil sensor is affected by the soil EC level. FIG. 9C is a comparison plot between the EC estimation results as measured by the soil sensor and the EC estimation results as measured by WARP with 2.4 GHz channels. It is shown that EC measured by WARP with 2.4 GHz channels is higher than EC measured by the soil sensor. FIG. 9D is a comparison plot between the soil permittivity estimation results as measured by the soil sensor and the soil permittivity estimation results as measured by WARP with 2.4 GHz channels. It is shown that the deviation is larger at higher salinity levels.

The measurements were conducted with WARP at 2.4 GHz and the Decagon GS3 soil sensor. For each data point in FIGS. 9A-D, the results of WARP were averaged at multiple heights of the transmit antenna from 0.15 m to 0.6 m and the results of the soil sensor at more than 10 locations around the antenna array. Soil moisture, soil solution, and soil type are three major factors that affect EC. Their impacts on EC are analyzed separately in the following discussion.

EC has a strong correlation with soil water content. Previous studies have observed a linear relationship between permittivity and EC. Here, the present inventors examined whether this relationship holds true in the system by varying soil moisture. The tap water added into the soil had an EC value of 0.006 S/m, which was measured by the Decagon GS3 soil sensor. FIG. 9A plots EC versus permittivity measured by the system at 2.4 GHz. EC of all tested soil types tends to increase as permittivity increases. Similar trends in permittivity and EC values measured by the soil sensor were observed as shown in FIG. 9B.

In practice, EC readings need to be normalized for different soil moisture values, to make EC maps reliable and repeatable. To enable normalization, the EC-permittivity relationship needs to be a one-to-one function. From this perspective, the system outperforms the soil sensor. As shown in FIG. 9B, the curves overlap in the high permittivity region, which means, that the same point in the high permittivity region can map to multiple EC values in the low permittivity region. In contrast, the one-to-one mapping is consistent in the system even in the high permittivity region. The poor performance of the soil sensor at high permittivity range is because it is a capacitance sensor, and its capacitance measurement is affected by its resistive part while its EC measurement that relies on resistance is accurate. When resistance or EC of soil is high, the sensor will measure a higher capacitance and hence a higher permittivity than the true value.

EC isolated from moisture variation can be converted to salinity, which has crucial meanings in precision agriculture. Here the system's capability of detecting different salinity levels of soil was evaluated. Three salinity levels were created by adding different amount of salt into three boxes with the same type of potting soil. By looking at EC values vertically with the same permittivity in FIG. 9A and FIG. 9B, it is observed that the system can successfully detect the increase of salinity levels from EC readings at all permittivity regions while the soil sensor can only tell the difference of salinity levels when permittivity is smaller than 20.

Different soil types may have different EC-permittivity and EC-salinity relationships due to dielectric property change. Previously, most of the experiments were conducted with potting soil since it is more accessible and hence easier to set up controlled experiments. Here two typical types of real soils were tested to show the accuracy of the system in detecting permittivity and EC of real-world soils. As shown in FIG. 9A and FIG. 9B, the three types of soils have quite different salinity levels. Generally, the system can detect the permittivity increase as water content increases and EC increase as salinity level increases in different types of soils. The rate of increase in EC over permittivity is different for different soil types and even for the same soil type with different salinity levels. In practice, the system is preferably calibrated for different soil types, just as the existing soil sensors have to be calibrated before use.

Soil EC measured by the system and soil EC measured by the soil sensor are plotted in FIG. 9C, and the soil permittivity measured by the soil measurement system and the soil permittivity measured by the soil sensor are plotted in FIG. 9D. Overall, the system measures a larger EC value and a smaller permittivity value than the soil sensor. The EC-EC slopes decrease as salinity level increases while the permittivity-permittivity slopes do not have a clear trend. The permittivity deviation is larger at larger moisture levels.

To compare the performance of WARP and Atheros Wi-Fi card, experiments were conducted with the same transmit and receive antenna locations for the same soil. The data transmit and record devices were changed from WARPs to Atheros WiFi cards. Very similar CSI phase results were seen as measured by WARP and Wi-Fi cards. While the Atheros Wi-Fi cards do not give as reliable amplitude measurements, the RSSI of the Atheros Wi-Fi cards reported for each channel can be used for EC estimation. The EC measured by Wi-Fi cards using RSSIs were similar to the EC measured by WARP. One example set of results is as follows: permittivity and EC measured by WARP is 8.8 and 0.24 S/m, while permittivity and EC measured by Wi-Fi is 9.2 and 0.21 S/m.

Previous studies show that both the real and imaginary parts of permittivity of soil are frequency dependent and affected by salinity, where the imaginary permittivity refers to the effective imaginary permittivity given as $\varepsilon''_{re}=\varepsilon''_r+\sigma/2\pi f\varepsilon_0$. In the frequency range from a few MHz to Wi-Fi frequency bands at 2.4 GHz, the real and imaginary parts of permittivity both drop over frequency while the imaginary drops more significantly at lower frequencies. As salinity increases, the real permittivity slightly drops while the imaginary permittivity increases and the increase is significant at lower frequencies. The difference of imaginary permittivity at lower frequencies and higher frequencies is due to the EC component $\sigma/2\pi f\varepsilon_0$. To evaluate how the system's relative ToF and relative amplitude-based permittivity and EC estimation match with existing studies, experiments were conducted with the soil sensor operating at 70 MHz, USRP operating at 400-1400 MHz, and WARP operating at 2.402-2.472 GHz. Both USRP and WARP use the multi-antenna system to measure relative ToF and amplitude. Since USRP measures a wide bandwidth, it is possible to get multiple data points by selecting subsets of frequency ranges within 400 to 1400 MHz.

Figure 10A:
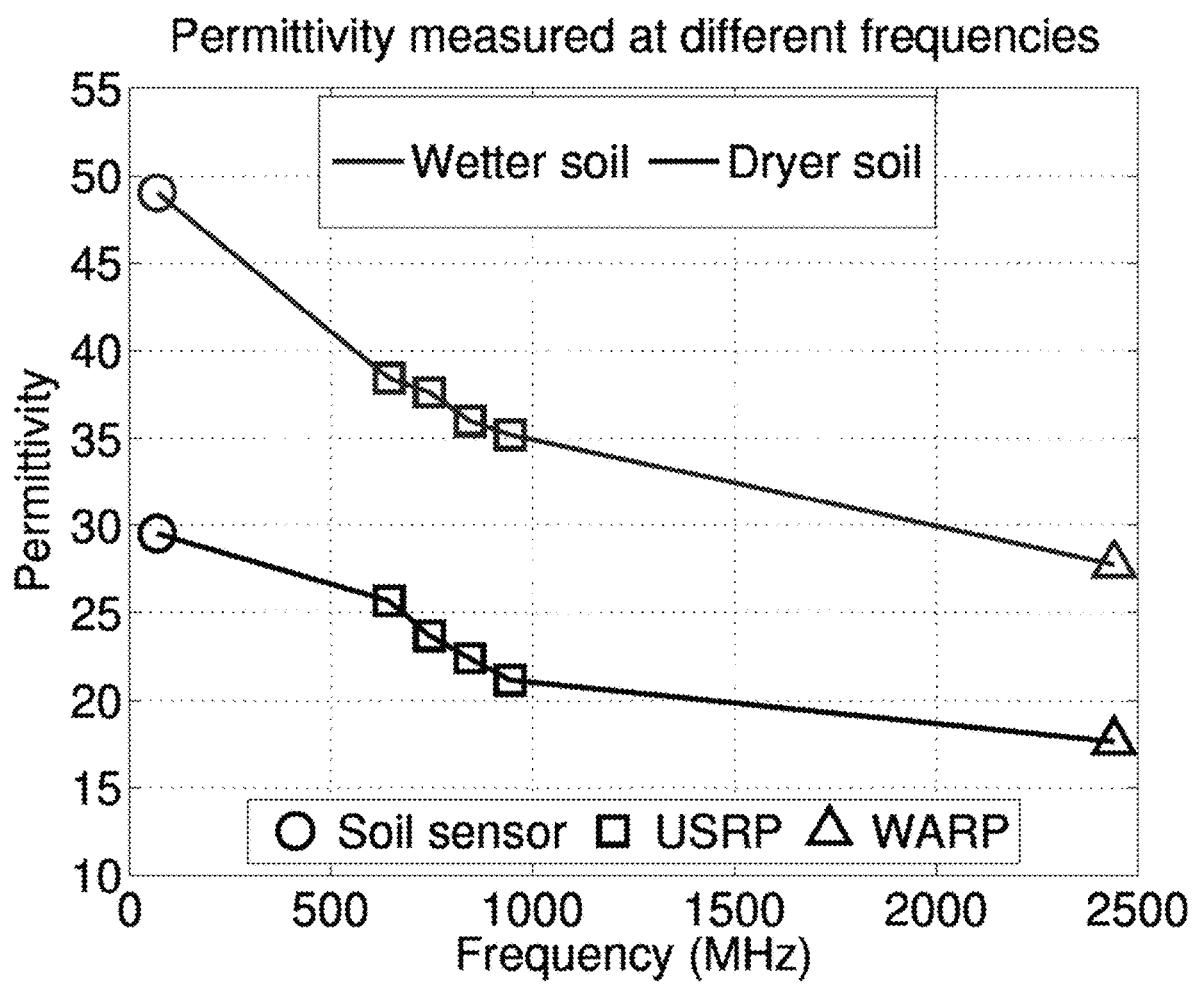
FIGS. 10A-10C plot soil permittivity, EC, and imaginary effective permittivity estimation results as measured by a soil sensor, Universal Software Radio Peripheral (USRP), and Wireless Open-Access Research Platform (WARP) at different frequencies.
Figure 10B:
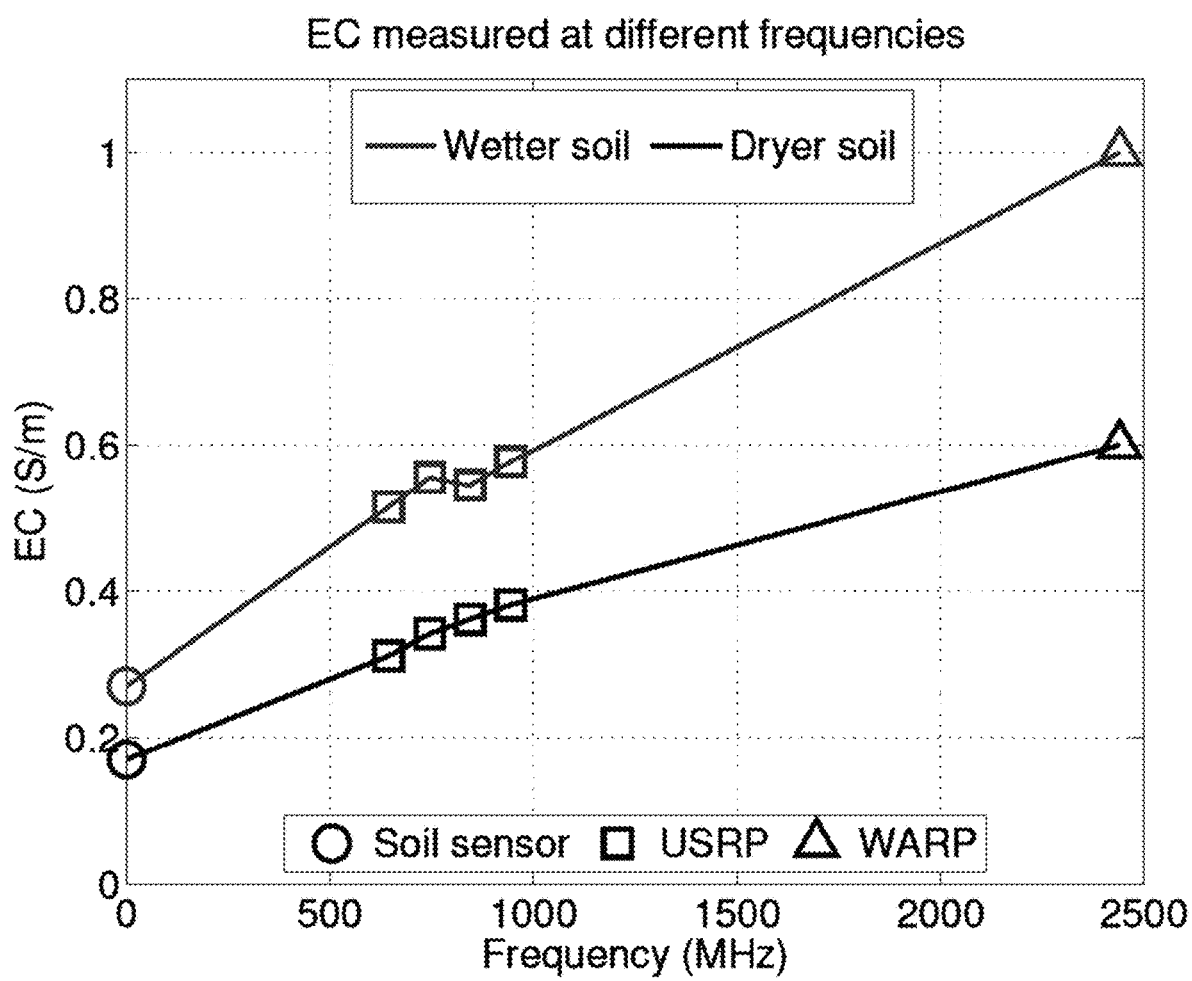
Figure 10C:
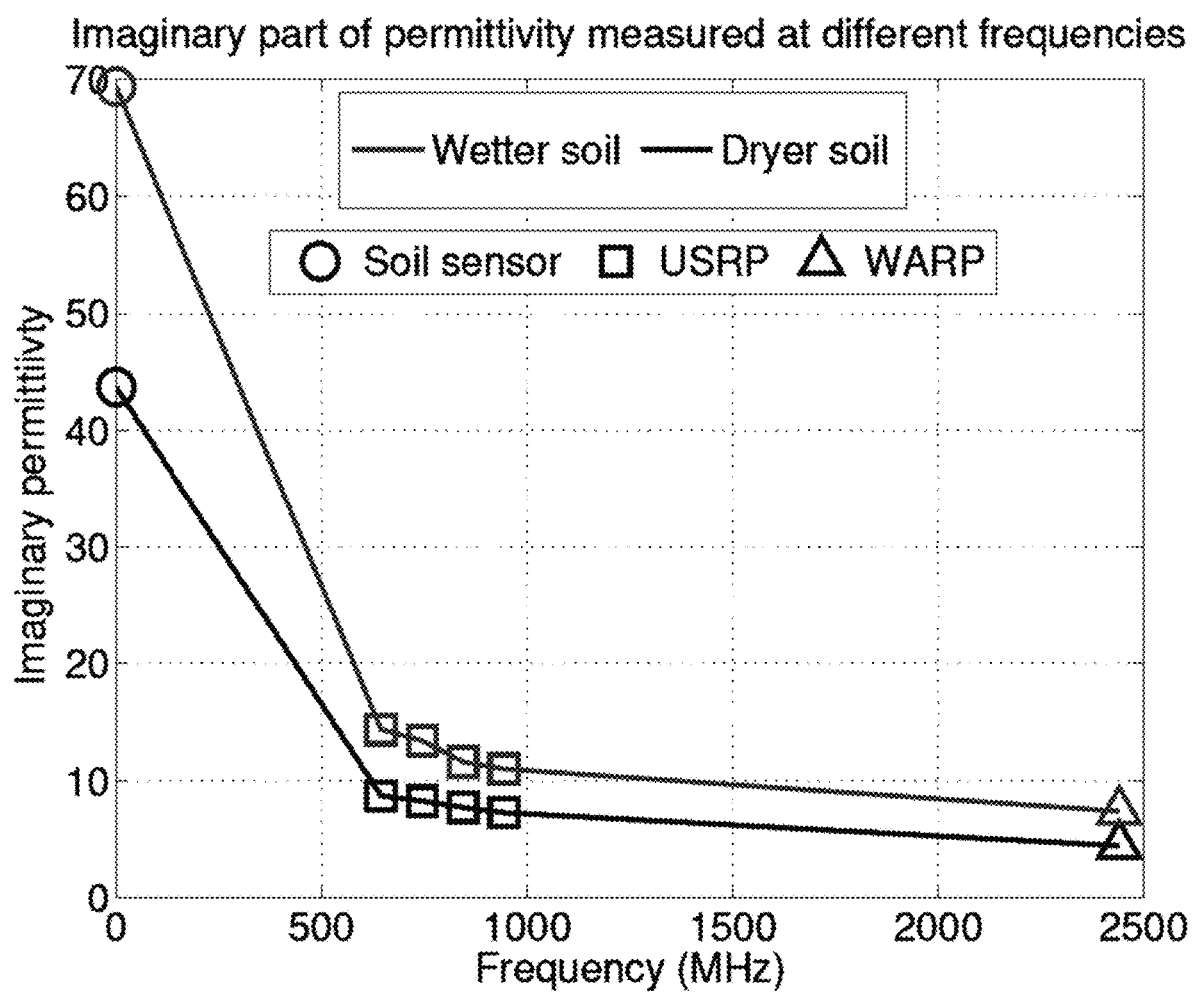

FIGS. 10A-C show the results of potting soil at two different moisture levels. FIG. 10A plots soil permittivity estimation results as measured by a soil sensor, USRP, and WARP at different frequencies. It is shown that apparent permittivity drops as frequency increases. FIG. 10B plots soil EC estimation results as measured by a soil sensor, USRP, and WARP at different frequencies. It is shown that EC increases as frequency increases. FIG. 10C plots soil imaginary effective permittivity estimation results, converted from soil EC results, as measured by a soil sensor, USRP, and WARP at different frequencies.

As frequency increases, the estimated permittivity decreases and EC increases, which agree with the deviations observed earlier. It will be noted that effective imaginary and effective EC, which is the measured EC value, are two interchangeable concepts and has a relationship of $\varepsilon''_{re}=\sigma_a/2\pi f\varepsilon_0$. The soil EC results were converted to soil imaginary effective permittivity in FIG. 10C for a more intuitive comparison with exiting studies.

The above analysis provides implications about how the soil measurement system is calibrated. (i) Getting the real part of permittivity from apparent permittivity measurement: as seen from FIG. 10C, the imaginary permittivity at 2.4 GHz is a small value compared with the real part of permittivity so the measured apparent permittivity is equal to the real part of permittivity and there is no need for calibration. (ii) Estimating soil water content from permittivity: the drop of real permittivity over frequency needs to be calibrated to use the existing water content-permittivity models which are mainly developed for lower frequencies. Fortunately, the dependence of real and imaginary permittivity on frequency has been modeled for different soil types, although measurements are still required to validate those models. (iii) Estimating salinity from measured EC: to get the true EC component, the imaginary permittivity component needs to be removed from the measured apparent EC. On the one hand, existing studies of soil dielectric properties can be referred to get the imaginary permittivity values for different soil types; on the other hand, the results in FIGS. 9A-C indicate that it is possible to directly convert the measured soil EC to salinity.

Figure 11:
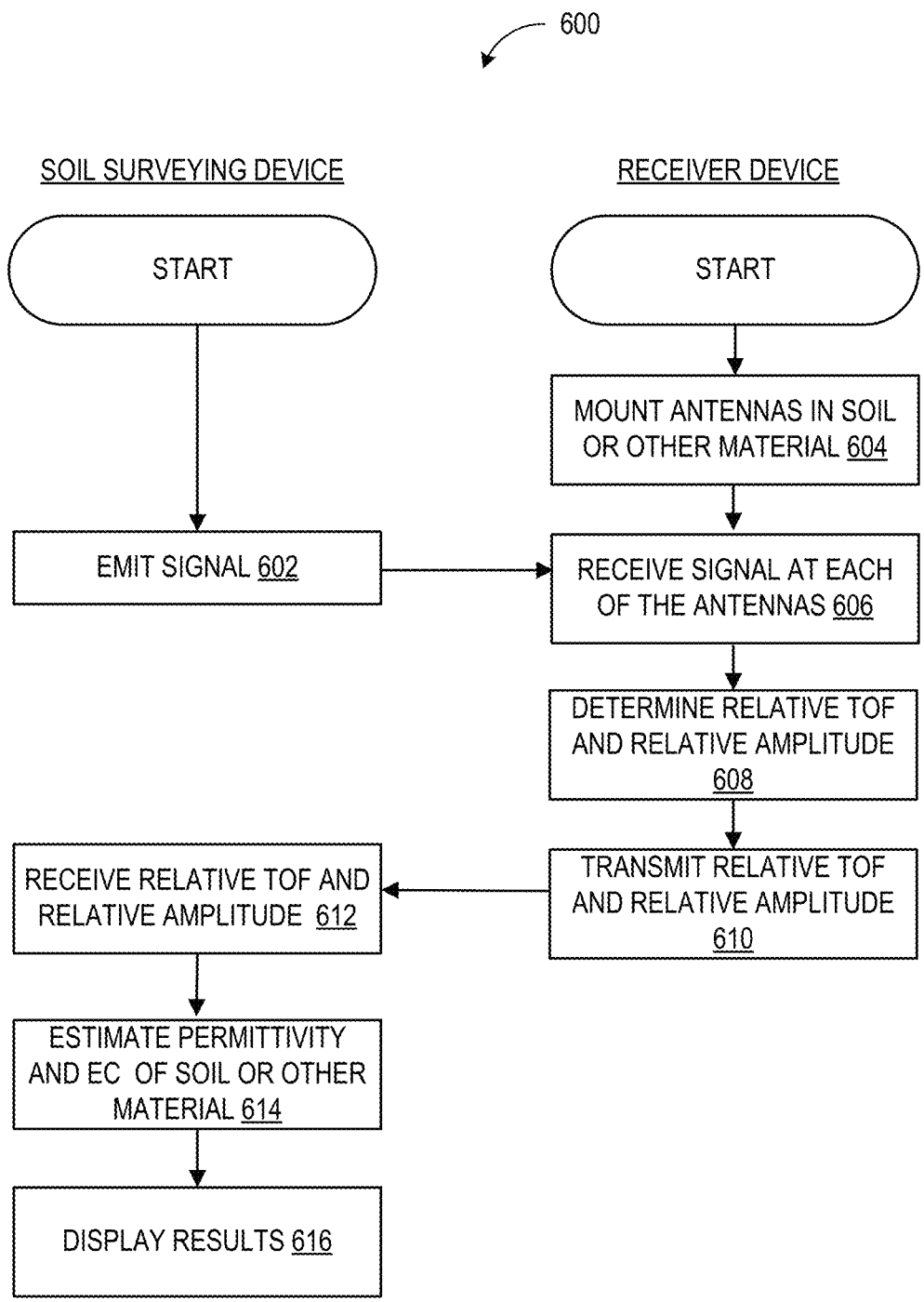
FIG. 11 shows a soil measurement method according to one implementation of the present disclosure.

FIG. 11 illustrates a method 600 for performing soil measurements. The following description of method 600 is provided with reference to the software and hardware components described above and shown in FIG. 1. It will be appreciated that method 600 also may be performed in other contexts using other suitable hardware and software components.

With reference to FIG. 11, at 604 the method may include mounting a plurality of subterranean antennas into a subterranean environment at different depths in the subterranean environment, the plurality of subterranean antennas electronically connected to a radio receiver. At 602 the method may include emitting a wireless signal via a wireless transmitter. At 606 the method may include receiving the wireless signal at each of the plurality of subterranean antennas in an array, each of the plurality of subterranean antennas receiving the wireless signal at a respective point in time. At 608 the method may include determining, via a processor, a relative ToF of the received wireless signal between the plurality of antennas at the respective point in time, and determining, via the processor, a relative amplitude or relative power at two of the plurality of antennas at different depths to estimate an attenuation coefficient. At 610 the method may include transmitting the relative ToF and relative amplitude to a downstream computing device, which is the soil surveying device. At 612 the method may include receiving the relative ToF and relative amplitude by the soil surveying device. At 612 the method may include estimating, via the processor, a soil permittivity based on the determined relative time of flight, and estimating a soil EC based on the estimated attenuation coefficient and the estimated soil permittivity. As described above, the soil electroconductivity may be estimated based on Equations (13) and $P_{rel}(\Delta d)=e^{2\alpha\Delta d}$, where $P_{rel}(\Delta d)$ is the relative amplitude or relative power, $\Delta d$ is a difference in depths between two of the plurality of subterranean antennas, $\alpha$ is the attenuation coefficient, $\varepsilon'_r$ is the estimated soil permittivity, and $\sigma_a$ is the soil electroconductivity. The soil permittivity may be estimated based on Equations (14), (15), and (19), where n is a soil refraction index, $K_a$ is the soil permittivity, $\Delta \tau$ is the relative time of flight, $\Delta l$ is a total path length difference between adjacent antennas, d is a distance between the antennas, $\theta_1$ is an angle of incidence of the wireless signal, and $\theta_4$ is an angle of the array. At 614 the method may include outputting the results including the estimated soil permittivity and the estimated soil EC via a display or communication interface communicatively coupled to the processor. In method 600, the soil surveying device is depicted as estimating the soil permittivity and soil EC, but it will be appreciated that in other embodiments, the receiver or another downstream computing device may alternatively estimate the soil permittivity and soil EC instead of the soil surveying device.

The soil measurement system overcomes the key challenge of limited bandwidth availability in the 2.4 GHz unlicensed spectrum using a novel multi-antenna technique that maps the propagation time and amplitude of Wi-Fi to the different antennas as a function of the refractivity and permittivity of soil, which in turn depend on soil moisture and EC. Experiments with two Software-defined radio (SDR) platforms (USRP and WARP), and two commodity Wi-Fi cards have shown that the soil measurement system can accurately estimate soil moisture and EC using Wi-Fi, thereby showing the potential of a future in which any farmer with a smartphone can sense soil in their farm without investing hundreds of dollars in soil sensing equipment.

Although the present disclosure is directed to a soil measurement system and method, it will be appreciated that the above measurement system and method may also implemented for the measurement of permittivity and EC of other materials and media besides soil, including but not limited to dry wall, concrete, brick, cinder-block, plaster, sand, asphalt, paint, mixes, wood, plastics, foams, and fiberglass, in applications where a plurality of antennas may be embedded into the material at different depths.

For example, the soil measurement system may be configured to be a material measurement system instead, comprising a material surveying device, a radio receiver, a plurality of antennas, and a processor. In such a material measurement system, the material surveying device also comprises a wireless radio transmitter configured to emit a wireless signal at a predetermined bandwidth in a predetermined spectrum, like a soil surveying device. Instead of being mounted in soil at different depths in the soil, the plurality of antennas in an array may be mounted in a material at different depths in the material. However, like the antennas and radio receiver of the soil measurement system, the plurality of antennas in an array in the material measurement system are electrically connected to the radio receiver, and each of the plurality of antennas is configured to receive the wireless signal at a respective point in time. Like the processor of the soil measurement system, the processor of the material measurement system is configured to determine a relative time of flight of the received wireless signal between the plurality of antennas at the respective point in time, and determine a relative amplitude or relative power at two of the plurality of antennas at different depths to estimate an attenuation coefficient. However, the processor of the material measurement system is configured to determine the properties of the material. Therefore, based on the determined relative time of flight, the processor estimates a permittivity of the material, and based on the estimated attenuation coefficient and the estimated permittivity of the material, the processor estimates an electroconductivity of the material. In addition to soil, the material may include but is not limited to dry wall, concrete, brick, cinder-block, plaster, sand, asphalt, paint, mixes, wood, plastics, foams, and fiberglass. Further, to estimate the permittivity, a machine learning model, such as described above, may be used which receives, as input, vectorized covariances matrices of channel state information (CSI) of the wireless signal, and outputs the estimated permittivity of the material.

In some embodiments, the methods and processes described herein may be tied to a computing system of one or more computing devices. In particular, such methods and processes may be implemented as a computer-application program or service, an application-programming interface (API), a library, and/or other computer-program product.

Figure 12:
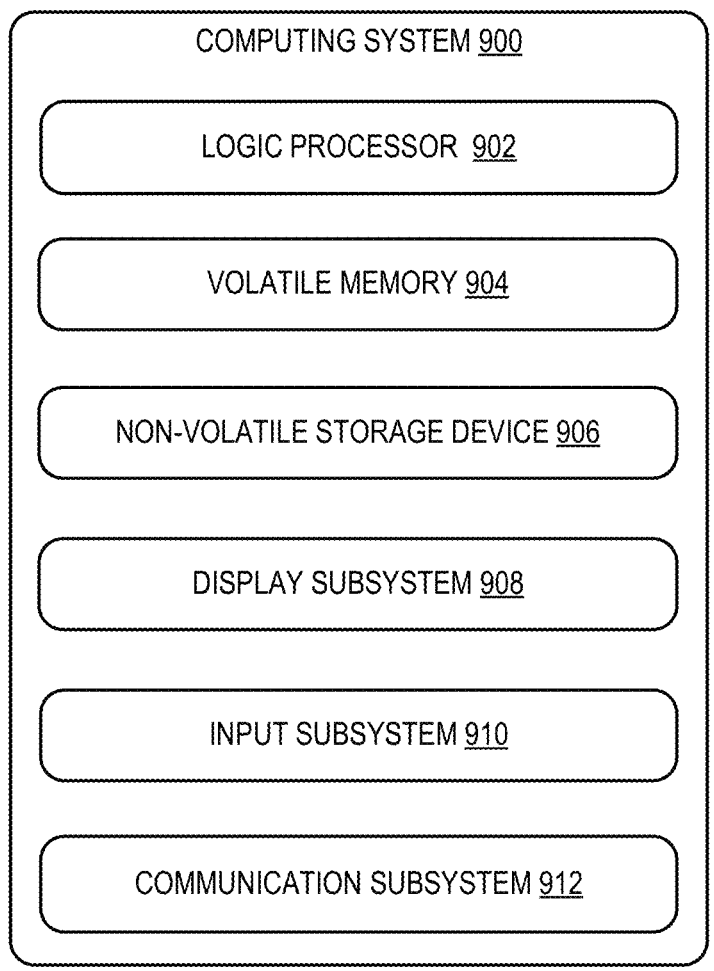
FIG. 12 shows a computing system according to an implementation of the present disclosure.

FIG. 12 schematically shows a non-limiting implementation of a computing system 900 that can enact one or more of the methods and processes described above. Computing system 900 is shown in simplified form. Computing system 900 may embody the soil surveying device 40 or receiver device 20 of FIG. 1. Computing system 900 may take the form of one or more personal computers, server computers, tablet computers, home-entertainment computers, network computing devices, gaming devices, mobile computing devices, mobile communication devices (e.g., smart phone), and/or other computing devices, and wearable computing devices such as smart wristwatches and head mounted augmented reality devices.

Computing system 900 includes a logic processor 902 volatile memory 904, and a non-volatile storage device 906. Computing system 900 may optionally include a display subsystem 908, input subsystem 910, communication subsystem 912, and/or other components not shown in FIG. 12.

Logic processor 902 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor may include one or more physical processors (hardware) configured to execute software instructions. Additionally or alternatively, the logic processor may include one or more hardware logic circuits or firmware devices configured to execute hardware-implemented logic or firmware instructions. Processors of the logic processor 902 may be single-core or multi-core, and the instructions executed thereon may be configured for sequential, parallel, and/or distributed processing. Individual components of the logic processor optionally may be distributed among two or more separate devices, which may be remotely located and/or configured for coordinated processing. Aspects of the logic processor may be virtualized and executed by remotely accessible, networked computing devices configured in a cloud-computing configuration. In such a case, these virtualized aspects are run on different physical logic processors of various different machines, it will be understood.

Non-volatile storage device 906 includes one or more physical devices configured to hold instructions executable by the logic processors to implement the methods and processes described herein. When such methods and processes are implemented, the state of non-volatile storage device 906 may be transformed—e.g., to hold different data.

Non-volatile storage device 906 may include physical devices that are removable and/or built-in. Non-volatile storage device 906 may include optical memory (e.g., CD, DVD, HD-DVD, Blu-Ray Disc, etc.), semiconductor memory (e.g., ROM, EPROM, EEPROM, FLASH memory, etc.), and/or magnetic memory (e.g., hard-disk drive, floppy-disk drive, tape drive, MRAM, etc.), or other mass storage device technology. Non-volatile storage device 906 may include nonvolatile, dynamic, static, read/write, read-only, sequential-access, location-addressable, file-addressable, and/or content-addressable devices. It will be appreciated that non-volatile storage device 906 is configured to hold instructions even when power is cut to the non-volatile storage device 906.

Volatile memory 904 may include physical devices that include random access memory. Volatile memory 904 is typically utilized by logic processor 902 to temporarily store information during processing of software instructions. It will be appreciated that volatile memory 904 typically does not continue to store instructions when power is cut to the volatile memory 904.

Aspects of logic processor 902, volatile memory 904, and non-volatile storage device 906 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module," "program," and "engine" may be used to describe an aspect of computing system 900 typically implemented in software by a processor to perform a particular function using portions of volatile memory, which function involves transformative processing that specially configures the processor to perform the function. Thus, a module, program, or engine may be instantiated via logic processor 902 executing instructions held by non-volatile storage device 906, using portions of volatile memory 904. It will be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" may encompass individual or groups of executable files, data files, libraries, drivers, scripts, database records, etc.

When included, display subsystem 908 may be used to present a visual representation of data held by non-volatile storage device 906. The visual representation may take the form of a graphical user interface (GUI). As the herein described methods and processes change the data held by the non-volatile storage device, and thus transform the state of the non-volatile storage device, the state of display subsystem 908 may likewise be transformed to visually represent changes in the underlying data. Display subsystem 908 may include one or more display devices utilizing virtually any type of technology. Such display devices may be combined with logic processor 902, volatile memory 904, and/or non-volatile storage device 906 in a shared enclosure, or such display devices may be peripheral display devices.

When included, input subsystem 910 may comprise or interface with one or more user-input devices such as a keyboard, mouse, touch screen, or game controller. In some implementations, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity; and/or any other suitable sensor.

When included, communication subsystem 912 may be configured to communicatively couple various computing devices described herein with each other, and with other devices. Communication subsystem 912 may include wired and/or wireless communication devices compatible with one or more different communication protocols. As non-limiting examples, the communication subsystem may be configured for communication via a wireless telephone network, or a wired or wireless local- or wide-area network, such as Bluetooth and HDMI over Wi-Fi connection. In some implementations, the communication subsystem may allow computing system 900 to send and/or receive messages to and/or from other devices via a network such as the Internet.

The following paragraphs provide additional support for the claims of the subject application. One aspect provides a soil measurement system comprising a soil surveying device comprising a wireless radio transmitter configured to emit a wireless signal at a predetermined bandwidth in a predetermined spectrum; a radio receiver; a plurality of subterranean antennas in an array electronically connected to the radio receiver and configured to be mounted in a subterranean environment at different depths in the subterranean environment, wherein each of the plurality of subterranean antennas is configured to receive the wireless signal at a respective point in time; and a processor configured to determine a relative time of flight of the received wireless signal between the plurality of subterranean antennas at the respective point in time; and estimate a soil permittivity based on the determined relative time of flight. In this aspect, additionally or alternatively, the processor may further be configured to transmit the estimated soil permittivity via a wireless or wired connection to a downstream computing device. In this aspect, additionally or alternatively, the soil surveying device may function as the downstream computing device. In this aspect, additionally or alternatively, a smartphone or tablet computer may be used as the soil surveying device that functions as the downstream computing device, and the wireless transmitter may be a WiFi transmitter equipped in a wireless network interface controller of the smartphone or tablet computer. In this aspect, additionally or alternatively, the downstream computing device may be configured to output the estimated soil permittivity via a display interface. In this aspect, additionally or alternatively, the wireless radio transmitter may be selected from the group consisting of universal software radio peripheral, wireless open-access research platform, and wireless network interface controller. In this aspect, additionally or alternatively, the processor may further be configured to determine a relative amplitude or relative power at two of the plurality of subterranean antennas at different depths to estimate an attenuation coefficient; and estimate a soil electroconductivity based on the estimated attenuation coefficient and the estimated soil permittivity. In this aspect, additionally or alternatively, the processor may further be configured to estimate a soil moisture level based on the estimated soil permittivity and/or the estimated soil electroconductivity. In this aspect, additionally or alternatively, the predetermined spectrum may be 2.4 GHz; and the predetermined bandwidth may be 70 MHz.

Another aspect provides a soil measurement method comprising mounting a plurality of subterranean antennas into a subterranean environment at different depths in the subterranean environment, the plurality of subterranean antennas electronically connected to a radio receiver; emitting a wireless signal at a predetermined bandwidth in a predetermined spectrum via a wireless radio transmitter; receiving the wireless signal at each of the plurality of subterranean antennas in an array, each of the plurality of subterranean antennas receiving the wireless signal at a respective point in time; determining, via a processor, a relative time of flight of the received wireless signal between the plurality of subterranean antennas at the respective point in time; estimating, via the processor, a soil permittivity based on the determined relative time of flight; and outputting the estimated soil permittivity via a display or communication interface communicatively coupled to the processor. In this aspect, additionally or alternatively, the method may further comprise determining, via the processor, a relative amplitude or relative power at two of the plurality of subterranean antennas at different depths to estimate an attenuation coefficient; and estimating a soil electroconductivity based on the estimated attenuation coefficient and the estimated soil permittivity. In this aspect, additionally or alternatively, the method may further comprise estimating a soil moisture level based on the estimated soil permittivity and/or the estimated soil electroconductivity. In this aspect, additionally or alternatively, the soil electroconductivity may be estimated based on Equation (13) and $P_{rel}(\Delta d) = e^{2\alpha \Delta d}$, where $P_{rel}(\Delta d)$ is the relative amplitude or relative power, $\Delta d$ is a difference in depths between two of the plurality of subterranean antennas, $\alpha$ is the attenuation coefficient, $\varepsilon'_r$ is the estimated soil permittivity, and $\sigma_a$ is the soil electroconductivity:

$$\sigma_a = \frac{\alpha \sqrt{\varepsilon'_r}}{60\pi}. \tag{13}$$

In this aspect, additionally or alternatively, the estimated soil electroconductivity may be normalized for the estimated soil permittivity based on an electroconductivity map establishing a one-to-one relationship between the soil electroconductivity and the soil permittivity. In this aspect, additionally or alternatively, the wireless radio transmitter may be selected from the group consisting of universal software radio peripheral, wireless open-access research platform, and wireless network interface controller. In this aspect, additionally or alternatively, the predetermined spectrum may be 2.4 GHz; and the predetermined bandwidth may be 70 MHz. In this aspect, additionally or alternatively, the soil permittivity is estimated based on Equations (14), (15), and (19), where n is a soil refraction index, $K_a$ is the soil permittivity, $\Delta\tau$ is the relative time of flight, $\Delta l$ is a total path length difference between adjacent antennas, d is a distance between the antennas, $\theta_1$ is an angle of incidence of the wireless signal, and $\theta_4$ is an angle of the array:

$$n = \sqrt{K_a}, \tag{14}$$

$$\Delta\tau = \Delta l/c, \tag{15}$$

$$\Delta l = nd\sin\left(\theta_4 - \arcsin\left(\frac{\sin\theta_1}{n}\right)\right). \tag{19}$$

Another aspect provides a material measurement system comprising a material surveying device comprising a wireless radio transmitter configured to emit a wireless signal at a predetermined bandwidth in a predetermined spectrum; a radio receiver; a plurality of antennas in an array electronically connected to the radio receiver and configured to be mounted in a material at different depths in the material, wherein each of the plurality of antennas is configured to receive the wireless signal at a respective point in time; and a processor configured to: determine a relative time of flight of the received wireless signal between the plurality of antennas at the respective point in time; and estimate a permittivity of the material based on the determined relative time of flight. In this aspect, additionally or alternatively, the processor may be further configured to determine a relative amplitude or relative power at two of the plurality of antennas at different depths to estimate an attenuation coefficient; estimate an electroconductivity of the material based on the estimated attenuation coefficient and the estimated permittivity of the material; and estimate a moisture level of the material based on the estimated permittivity and/or the estimated electroconductivity of the material. In this aspect, additionally or alternatively, to estimate the permittivity, a machine learning model may be used which receives, as input, vectorized covariances matrices of channel state information (CSI) of the wireless signal, and outputs the estimated permittivity.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A soil measurement system, comprising:
a soil surveying device comprising a wireless radio transmitter configured to emit a wireless signal at a predetermined bandwidth in a predetermined spectrum;
a radio receiver;
a plurality of subterranean antennas in an array electronically connected to the radio receiver and configured to be mounted in a subterranean environment at different depths in the subterranean environment, wherein each of the plurality of subterranean antennas is configured to receive the wireless signal at a respective point in time; and a processor configured to:
  determine a relative time of flight of the received wireless signal between the plurality of subterranean antennas at the respective point in time; and
  estimate a soil permittivity based on the determined relative time of flight.

2. The soil measurement system of claim 1, wherein the processor is further configured to:
  transmit the estimated soil permittivity via a wireless or wired connection to a downstream computing device.

3. The soil measurement system of claim 2, wherein the soil surveying device functions as the downstream computing device.

4. The soil measurement system of claim 3, wherein a smartphone or tablet computer is used as the soil surveying device that functions as the downstream computing device, and the wireless radio transmitter is a WiFi transmitter equipped in a wireless network interface controller of the smartphone or tablet computer.

5. The soil measurement system of claim 2, wherein the downstream computing device is configured to output the estimated soil permittivity via a display interface.

6. The soil measurement system of claim 1, wherein the wireless radio transmitter is selected from the group consisting of universal software radio peripheral, wireless open-access research platform, and wireless network interface controller.

7. The soil measurement system of claim 1, wherein the processor is further configured to:
  determine a relative amplitude or relative power at two of the plurality of subterranean antennas at different depths to estimate an attenuation coefficient; and
  estimate a soil electroconductivity based on the estimated attenuation coefficient and the estimated soil permittivity.

8. The soil measurement system of claim 7, wherein the processor is further configured to:
  estimate a soil moisture level based on the estimated soil permittivity and/or the estimated soil electroconductivity.

9. The soil measurement system of claim 1, wherein
  the predetermined spectrum is 2.4 GHz; and
  the predetermined bandwidth is 70 MHz.

10. A soil measurement method, comprising:
  mounting a plurality of subterranean antennas into a subterranean environment at different depths in the subterranean environment, the plurality of subterranean antennas electronically connected to a radio receiver;
  emitting a wireless signal at a predetermined bandwidth in a predetermined spectrum via a wireless radio transmitter;
  receiving the wireless signal at each of the plurality of subterranean antennas in an array, each of the plurality of subterranean antennas receiving the wireless signal at a respective point in time;
  determining, via a processor, a relative time of flight of the received wireless signal between the plurality of subterranean antennas at the respective point in time;
  estimating, via the processor, a soil permittivity based on the determined relative time of flight; and
  outputting the estimated soil permittivity via a display or communication interface communicatively coupled to the processor.

11. The soil measurement method of claim 10, further comprising:
  determining, via the processor, a relative amplitude or relative power at two of the plurality of subterranean antennas at different depths to estimate an attenuation coefficient; and
  estimating a soil electroconductivity based on the estimated attenuation coefficient and the estimated soil permittivity.

12. The soil measurement method of claim 11, further comprising:
  estimating a soil moisture level based on the estimated soil permittivity and/or the estimated soil electroconductivity.

13. The soil measurement method of claim 11, wherein the soil electroconductivity is estimated based on Equation (13) and $P_{rel}(\Delta d)=e^{2\alpha \Delta d}$, where $P_{rel}(\Delta d)$ is the relative amplitude or relative power, $\Delta d$ is a difference in depths between two of the plurality of subterranean antennas, $\alpha$ is the attenuation coefficient, $\varepsilon'_r$ is the estimated soil permittivity, and $\sigma_a$ is the soil electroconductivity:

$$\sigma_a = \frac{\alpha \sqrt{\varepsilon'_r}}{60\pi}. \qquad (13)$$

14. The soil measurement method of claim 11, wherein the estimated soil electroconductivity is normalized for the estimated soil permittivity based on an electroconductivity map establishing a one-to-one relationship between the soil electroconductivity and the soil permittivity.

15. The soil measurement method of claim 10, wherein the wireless radio transmitter is selected from the group consisting of universal software radio peripheral, wireless open-access research platform, and wireless network interface controller.

16. The soil measurement method of claim 10, wherein
  the predetermined spectrum is 2.4 GHz; and
  the predetermined bandwidth is 70 MHz.

17. The soil measurement method of claim 10, wherein the soil permittivity is estimated based on Equations (14), (15), and (19), where n is a soil refraction index, $K_a$ is the soil permittivity, $\Delta\tau$ is the relative time of flight, $\Delta l$ is a total path length difference between adjacent antennas, d is a distance between the antennas, $\theta_1$ is an angle of incidence of the wireless signal, and $\theta_4$ is an angle of the array:

$$n = \sqrt{K_a} \qquad (14)$$

$$\Delta\tau = \frac{\Delta l}{c} \qquad (15)$$

$$\Delta l = nd\sin\left(\theta_4 - \arcsin\left(\frac{\sin\theta_1}{n}\right)\right). \qquad (19)$$

18. A material measurement system, comprising:
  a material surveying device comprising a wireless radio transmitter configured to emit a wireless signal at a predetermined bandwidth in a predetermined spectrum;
  a radio receiver;
  a plurality of antennas in an array electronically connected to the radio receiver and configured to be mounted in a material at different depths in the material, wherein each of the plurality of antennas is configured to receive the wireless signal at a respective point in time; and a processor configured to:
  determine a relative time of flight of the received wireless signal between the plurality of antennas at the respective point in time; and
  estimate a permittivity of the material based on the determined relative time of flight.

19. The material measurement system of claim 18, wherein the processor is further configured to:
  determine a relative amplitude or relative power at two of the plurality of antennas at different depths to estimate an attenuation coefficient;
  estimate an electroconductivity of the material based on the estimated attenuation coefficient and the estimated permittivity of the material; and
  estimate a moisture level of the material based on the estimated permittivity and/or the estimated electroconductivity of the material.

20. The material measurement system of claim 18, wherein
  to estimate the permittivity, a machine learning model is used which receives, as input, vectorized covariances matrices of channel state information (CSI) of the wireless signal, and outputs the estimated permittivity.

* * * * *